(12) United States Patent
Sungail et al.

(10) Patent No.: US 12,226,827 B2
(45) Date of Patent: Feb. 18, 2025

(54) SPHERICAL TANTALUM POWDER, PRODUCTS CONTAINING THE SAME, AND METHODS OF MAKING THE SAME

(71) Applicant: Global Advanced Metals USA, Inc., Wellesley Hills, MA (US)

(72) Inventors: Craig M. Sungail, Chadds Ford, PA (US); Aamir Dawood Abid, Spring City, PA (US)

(73) Assignee: GLOBAL ADVANCED METALS USA, INC., Wellesley Hills, MA (US)

( * ) Notice: Subject to any disclaimer, the term of this patent is extended or adjusted under 35 U.S.C. 154(b) by 0 days.

(21) Appl. No.: 18/198,300

(22) Filed: May 17, 2023

(65) Prior Publication Data

US 2023/0286043 A1     Sep. 14, 2023

Related U.S. Application Data

(63) Continuation of application No. 16/286,683, filed on Feb. 27, 2019, now Pat. No. 11,691,197.
(Continued)

(51) Int. Cl.
    *B22F 3/11*       (2006.01)
    *B22F 1/052*     (2022.01)
(Continued)

(52) U.S. Cl.
    CPC ............... *B22F 3/11* (2013.01); *B22F 1/052* (2022.01); *B22F 1/065* (2022.01); *B22F 1/142* (2022.01); *B22F 10/34* (2021.01); *B33Y 70/00* (2014.12); *B22F 10/12* (2021.01); *B22F 10/14* (2021.01); *B22F 10/25* (2021.01); *B22F 10/28* (2021.01); *B22F 10/32* (2021.01); *B22F 10/36* (2021.01);
(Continued)

(58) Field of Classification Search
    CPC ...... B22F 2301/20; B22F 1/065; B22F 1/142; B22F 1/052; B33Y 70/00; B33Y 80/00
See application file for complete search history.

(56) References Cited

U.S. PATENT DOCUMENTS 2,950,185 A     8/1960   Hellier et al.
3,767,456 A    10/1973   Glaski
(Continued)

FOREIGN PATENT DOCUMENTS

CN          1899730 A      1/2007
CN       107598166 A      1/2018
(Continued)

OTHER PUBLICATIONS

Zi et al. ("Spheroidisation of tungsten powder by radio frequency plasma for selective laser melting." Materials Science and Technology 34.6 (2018): 735-742.) (Year: 2018).*
(Continued)

*Primary Examiner* — Ricardo D Morales
(74) *Attorney, Agent, or Firm* — Kilyk & Bowersox, P.L.L.C.

(57) ABSTRACT

Tantalum powder that is highly spherical is described. The tantalum powder can be useful in additive manufacturing and other uses. Methods to make the tantalum powder are further described as well as methods to utilize the tantalum powder in additive manufacturing processes. Resulting products and articles using the tantalum powder are further described.

38 Claims, 4 Drawing Sheets

Related U.S. Application Data

(60) Provisional application No. 62/793,418, filed on Jan. 17, 2019, provisional application No. 62/638,328, filed on Mar. 5, 2018.

(51) Int. Cl.
| | |
|---|---|
| *B22F 1/065* | (2022.01) |
| *B22F 1/142* | (2022.01) |
| *B22F 10/12* | (2021.01) |
| *B22F 10/14* | (2021.01) |
| *B22F 10/25* | (2021.01) |
| *B22F 10/28* | (2021.01) |
| *B22F 10/32* | (2021.01) |
| *B22F 10/34* | (2021.01) |
| *B22F 10/36* | (2021.01) |
| *B22F 10/64* | (2021.01) |
| *B22F 12/13* | (2021.01) |
| *B33Y 70/00* | (2020.01) |
| *B33Y 80/00* | (2015.01) |

(52) U.S. Cl.
CPC .............. *B22F 10/64* (2021.01); *B22F 12/13* (2021.01); *B22F 2301/20* (2013.01); *B22F 2304/10* (2013.01); *B33Y 80/00* (2014.12)

(56) References Cited

U.S. PATENT DOCUMENTS

| | | |
|---|---|---|
| 3,829,310 A | 8/1974 | Mahy |
| 4,062,678 A | 12/1977 | Dreyer et al. |
| 4,067,736 A | 1/1978 | Vartanian |
| 4,149,876 A | 4/1979 | Rerat |
| 4,684,399 A | 8/1987 | Bergman et al. |
| 4,805,704 A | 2/1989 | Kobashi et al. |
| 4,940,490 A | 7/1990 | Fife et al. |
| 4,945,452 A | 7/1990 | Sturmer et al. |
| 5,200,595 A | 4/1993 | Boulos et al. |
| 5,211,741 A | 5/1993 | Fife |
| 5,217,526 A | 6/1993 | Fife |
| 5,234,491 A | 8/1993 | Chang |
| 5,242,481 A | 9/1993 | Kumar |
| 5,245,514 A | 9/1993 | Fife et al. |
| 5,306,462 A | 4/1994 | Fife |
| 5,412,533 A | 5/1995 | Murayama et al. |
| 5,448,447 A | 9/1995 | Chang |
| 5,498,446 A | 3/1996 | Axelbaum et al. |
| 5,580,367 A | 12/1996 | Fife |
| 5,580,516 A | 12/1996 | Kumar |
| 5,837,121 A | 11/1998 | Kinard et al. |
| 5,935,408 A | 8/1999 | Kinard et al. |
| 5,993,513 A | 11/1999 | Fife |
| 6,051,044 A | 4/2000 | Fife |
| 6,072,694 A | 6/2000 | Hahn et al. |
| 6,136,176 A | 10/2000 | Wheeler et al. |
| 6,162,345 A | 12/2000 | Kinard et al. |
| 6,191,013 B1 | 2/2001 | Hahn et al. |
| 6,312,642 B1 | 11/2001 | Fife |
| 6,322,912 B1 | 11/2001 | Fife |
| 6,328,927 B1 | 12/2001 | Lo et al. |
| 6,338,816 B1 | 1/2002 | Fife |
| 6,348,113 B1 | 2/2002 | Michaluk et al. |
| 6,373,685 B1 | 4/2002 | Kimmel et al. |
| 6,375,704 B1 | 4/2002 | Habecker et al. |
| 6,391,275 B1 | 5/2002 | Fife |
| 6,416,730 B1 | 7/2002 | Fife |
| 6,420,043 B1 | 7/2002 | Fife et al. |
| 6,462,934 B2 | 10/2002 | Kimmel et al. |
| 6,527,937 B2 | 3/2003 | Fife |
| 6,576,099 B2 | 6/2003 | Kimmel et al. |
| 6,582,641 B1 | 6/2003 | Lo et al. |
| 6,616,623 B1 | 9/2003 | Kutushov |
| 6,639,787 B2 | 10/2003 | Kimmel et al. |
| 6,643,121 B1 | 11/2003 | Huntington |
| 6,699,757 B1 | 3/2004 | Hwang |
| 6,699,767 B1 | 3/2004 | Huntington |
| 6,759,026 B2 | 7/2004 | Kimmel et al. |
| 6,770,154 B2 | 8/2004 | Koenigsmann et al. |
| 6,788,523 B1 | 9/2004 | Hossick-Schott et al. |
| 6,804,109 B1 | 10/2004 | Hahn et al. |
| 6,813,140 B1 | 11/2004 | Huntington |
| 6,849,292 B1 | 2/2005 | Huntington |
| 6,870,727 B2 | 3/2005 | Edson et al. |
| 6,896,782 B2 | 5/2005 | Melody et al. |
| 7,081,148 B2 | 7/2006 | Koenigsmann et al. |
| 7,172,985 B2 | 2/2007 | Pinceloup et al. |
| 7,190,571 B2 | 3/2007 | Heusmann et al. |
| 7,220,397 B2 | 5/2007 | Kimmel et al. |
| 7,241,436 B2 | 7/2007 | Fife |
| 7,442,227 B2 | 10/2008 | Rosen et al. |
| 7,445,679 B2 | 11/2008 | Koenitzer et al. |
| 7,445,762 B2 | 11/2008 | Fife |
| 7,485,198 B2 | 2/2009 | Michaluk |
| 7,515,397 B2 | 4/2009 | Reed et al. |
| 7,572,315 B2 | 8/2009 | Boulos et al. |
| 7,601,296 B2 | 10/2009 | Michaluk et al. |
| 7,655,214 B2 | 2/2010 | Reed et al. |
| 7,803,235 B2 | 9/2010 | Venigalla |
| 8,040,060 B2 | 10/2011 | Fukasawa et al. |
| 8,110,172 B2 | 2/2012 | Reed et al. |
| 8,168,118 B2 | 5/2012 | Michaluk et al. |
| 8,657,915 B2 | 2/2014 | Mizusaki et al. |
| 9,725,793 B2 | 8/2017 | Aimone et al. |
| 9,957,592 B2 | 5/2018 | Aimone et al. |
| 10,413,427 B2 | 9/2019 | Trieu |
| 10,422,025 B2 | 9/2019 | Aimone et al. |
| 10,943,744 B2 | 3/2021 | Sungail et al. |
| 11,393,638 B2 | 7/2022 | Krause et al. |
| 11,508,529 B2 | 11/2022 | Sungail et al. |
| 2003/0019326 A1* | 1/2003 | Han .................... C23C 14/3414 |
| | | 419/49 |
| 2004/0262157 A1 | 12/2004 | Ford et al. |
| 2005/0171615 A1* | 8/2005 | Georgette ............ A61C 8/0013 |
| | | 623/23.57 |
| 2011/0143042 A1* | 6/2011 | Peretti ....................... C23C 4/12 |
| | | 427/398.1 |
| 2012/0292814 A1* | 11/2012 | Spratt ................... A61F 2/4465 |
| | | 264/259 |
| 2015/0030493 A1* | 1/2015 | Scott ....................... B22F 10/25 |
| | | 264/41 |
| 2015/0162172 A1 | 6/2015 | Lo et al. |
| 2015/0292081 A1 | 10/2015 | Hogan et al. |
| 2016/0074942 A1 | 3/2016 | Fang et al. |
| 2018/0258512 A1* | 9/2018 | Sing ...................... B33Y 10/00 |
| 2018/0361479 A1* | 12/2018 | Tozzi ......................... B22F 5/04 |
| 2019/0271068 A1 | 9/2019 | Sungail et al. |
| 2020/0046510 A1 | 2/2020 | Maale |
| 2020/0046512 A1 | 2/2020 | Newman et al. |
| 2020/0048746 A1 | 2/2020 | Aimone et al. |
| 2020/0078861 A1 | 3/2020 | Sungail et al. |
| 2021/0016348 A1 | 1/2021 | Sungail et al. |
| 2022/0023942 A1 | 1/2022 | Sungail et al. |

FOREIGN PATENT DOCUMENTS

| | | |
|---|---|---|
| CN | 108500281 A | 9/2018 |
| EP | 0528974 B1 | 7/1997 |
| JP | 2004091843 A | 3/2004 |
| JP | 2005336617 A | 12/2005 |
| KR | 20110112591 A | 10/2011 |
| KR | 20170007359 A | 1/2017 |
| KR | 101800396 B1 | 12/2017 |
| WO | 2017048199 A1 | 3/2017 |
| WO | 2018050473 A1 | 3/2018 |
| WO | 2019197376 A1 | 10/2019 |

OTHER PUBLICATIONS

Scheck et al. ("Technical overview of additive manufacturing." Naval Surface Warfare Center, Carderock Division. NSWCCD-61-TR-2014/16.(Apr. 2014) (2014).). (Year: 2014).*

(56) References Cited

OTHER PUBLICATIONS

Morgan et al. ("Support structure development and initial results for metal powder bed fusion additive manufacturing." Procedia Manufacturing 10 (2017): 819-830.). (Year: 2017).*

Alec, "Researchers use titanium-tantalum alloy to improve stress absorption of 3D printed implants," 3D printer and 3D printing news, 2016.

Barr et al., "Processing Salt-encapsulated Tantalum Nanoparticles for High Purity, Ultra High Surface Area Applications," Journal Nanoparticles Research, 2006, vol. 8, pp. 11-22.

Boulos, "Plasma power can make better powders," Elsevier Ltd., 2004, vol. 59, Issue 5, pp. 16-21.

Yang et al., "Control of the Nano-Particle Weight Ratio in Stainless Steel Micro and Nano Powders by Radio Frequency Plasma Treatment," Metals, 2015, vol. 5, pp. 2058-2069.

Yang et al., "Preparation of Spherical Titanium Powders from Polygonal Titanium Hydride Powders by Radio Frequency Plasma Treatment," Materials Transactions, 2013, vol. 54, No. 12, pp. 2313-2316.

www.globaladvancedmetals.com/our-products/additive-manufacturing.aspx (2018).

Strauss et al., "Investigation Of Using Laser-Beam Powder-Bed-Fusion With A Mixture Of Powders to Achieve In-Situ Alloying," vol. 55, No. 2, 2019, pp. 43-50 (8 pages).

Nanyang Technological University, Singapore, Tech Offers "Novel Titanium based alloy for better orthopaedic implants," https://sc3dp.ntu.edu.sg/Research/Tech-Offers/Pages/Novel-titanium-based-alloy-for-better-orthopaedic-implants.aspx, Feb. 25, 2020, (2 pages).

Office Action issued in corresponding Japanese Patent Application No. 2020-546438 dated Oct. 27, 2021 (with English translation) (10 pages).

Office Action issued in corresponding Chinese Patent Application No. 201980017016.4 issued Feb. 28, 2022 (English translation only) (8 pages).

Office Action issued in corresponding Korean Patent Application No. 10-2020-7027720 issued May 3, 2022 (with English translation) (11 pages).

Francis, "Materials processing: a unified approach to processing of metals, ceramics and polymers," Academic Press, 2015, Chapter 5, pp. 343-415.

Zi et al., "Spheroidisation of tungsten powder by radio frequency plasma for selective laser melting," Materials Science and Technology, 2017, vol. 4, No. 6, pp. 735-742.

International Search Report and Written Opinion issued in corresponding International Patent Application No. PCT/US2019/019698 dated May 20, 2020 (13 pages).

Webb PA, "Volume and Density Determinations for Particle Technologists," www.micromeritics. com/pdf/app_articles/density _determinations.pdf, XP-002495931, Micromeritics Instrument Corp. Feb. 16, 2001, pp. 1-16.

* cited by examiner

TA-AM-T13

TA-AM-T14

SPHERICAL TANTALUM POWDER, PRODUCTS CONTAINING THE SAME, AND METHODS OF MAKING THE SAME

This application is a continuation of U.S. patent application Ser. No. 16/286,683 filed Feb. 27, 2019, which in turn claims the benefit under 35 U.S.C. § 119(e) of prior U.S. Provisional Patent Application No. 62/638,328 filed Mar. 5, 2018; and U.S. Provisional Patent Application No. 62/793,418 filed Jan. 17, 2019, which are incorporated in their entireties by reference herein.

BACKGROUND OF THE INVENTION

The present invention relates to metals, in particular tantalum, and products made from tantalum as well as methods of making and processing the tantalum.

Among its many applications, valve metal powder, such as tantalum powder, is generally used to produce capacitor electrodes, but has other uses outside of this industry, such as in the sputtering target industry, munition area, space industry and in view of its properties, tantalum has promise in the medical and dental implant areas.

Currently, for example, tantalum powders are generally produced via one of two methods: a mechanical process or a chemical process. The mechanical process includes the steps of electron beam melting of tantalum to form an ingot, hydriding the ingot, milling the hydride, and then dehydriding, crushing, and heat treating. This process generally produces powder with high purity.

The other generally utilized process for producing tantalum powder is a chemical process. Several chemical methods for producing tantalum powders are known in the art. U.S. Pat. No. 4,067,736, issued to Vartanian, and U.S. Pat. No. 4,149,876, issued to Rerat, relate to the chemical production process involving sodium reduction of potassium fluorotantalate ($K_2TaF_7$). A review of typical techniques is also described in the background sections of U.S. Pat. No. 4,684,399, issued to Bergman et al., and U.S. Pat. No. 5,234,491, issued to Chang. All patents and publications are incorporated in their entirety by reference herein.

Tantalum powders produced by chemical methods, for example, are well-suited for use in capacitors because they generally have larger surface areas than powders produced by mechanical methods. The chemical methods generally involve the chemical reduction of a tantalum compound with a reducing agent. Typical reducing agents include hydrogen and active metals such as sodium, potassium, magnesium, and calcium. Typical tantalum compounds include, but are not limited to, potassium fluorotantalate ($K_2TaF_7$), sodium fluorotantalate ($Na_2TaF_7$), tantalum pentachloride ($TaCl_5$), tantalum pentafluoride ($TaF_5$), and mixtures thereof. The most prevalent chemical process is the reduction of $K_2TaF_7$ with liquid sodium.

In the chemical reduction of a valve metal powder, such as tantalum powder, potassium fluorotantalate is recovered, melted, and reduced to tantalum metal powder by sodium reduction. Dried tantalum powder can then be recovered, and optionally thermally agglomerated under vacuum to avoid oxidation of the tantalum, and crushed. As the oxygen concentration of the valve metal material can be important in the production of capacitors, the granular powder typically is then deoxidized at elevated temperatures (e.g., up to about 1000° C. or higher) in the presence of a getter material, such as an alkaline earth metal (e.g., magnesium), that has a higher affinity for oxygen than the valve metal. A post-deoxidation process acid leaching conducted under normal atmospheric conditions (e.g., approximately 760 mm Hg) can be performed using a mineral acid solution including, for example, sulfuric acid or nitric acid, to dissolve metal and refractory oxide contaminants (e.g., magnesium and magnesium oxide contaminants) before the material is further processed. The acid leached powders are washed and dried, and may then be compressed, sintered, and anodized in conventional manners to make sintered porous bodies, such as anodes for capacitors.

Most of the efforts in developing tantalum powders has been driven by the capacitor anode industry, where powders were made for this specific purpose only. However, one or more properties of a tantalum powder for use in the capacitor industry can be generally unwanted in other industries such as in additive manufacturing. Such 'capacitor grade' tantalum powders can be unsuited or less suitable for such additive manufacturing. Accordingly, there is a need and desire to develop tantalum powders that can be useful in additive manufacturing and/or other industries.

SUMMARY OF THE PRESENT INVENTION

A feature of the present invention is to provide a tantalum powder that can be very useful in additive manufacturing or 3D printing.

Another feature of the present invention is to provide articles, products, and/or components from additive manufacturing or 3D printing using tantalum powder that is easier to use and/or provides one or more improved properties in such processes.

An additional feature of the present invention is to provide processes to make the tantalum powder as well as the articles, products, and/or components containing the tantalum powder.

Additional features and advantages of the present invention will be set forth in part in the description which follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purpose of the present invention, as embodied and broadly described herein, the present invention relates to tantalum powder. The tantalum powder includes a spherical shape wherein the powder has an average aspect ratio of from 1.0 to 1.25; a purity of tantalum of at least 99.9 wt % Ta based on total weight of the tantalum powder, excluding gas impurities; an average particle size of from about 0.5 micron to about 250 microns; a true density of from 16 g/cc to 16.6 g/cc; an apparent density of from about 4 g/cc to about 12.6 g/cc; and a Hall flow rate of 20 sec or less. The tantalum powder can be, and preferably is plasma heat-treated.

The present invention further relates to an article or an article of manufacture (or portion thereof or part thereof) made from or formed from the tantalum powder of the present invention. The article or portion thereof or part thereof can be, but is not limited to, a boss for a coil set for a physical vapor deposition process, a boss that comprises open cellular structures and solid structures, a coil set or part thereof for a physical vapor deposition process, an orthopedic implant or part thereof, a dental implant or part thereof, and other medical implants or portions thereof.

Further, the present invention relates to a method to make the tantalum powder of the present invention. The method can include plasma heat-treating a starting tantalum powder to at least partially melt at least an outer surface of said starting tantalum powder in an inert atmosphere to obtain a heat-treated tantalum powder, and cooling the heat-treated tantalum powder in an inert atmosphere to obtain the tantalum powder. The starting tantalum powder can be a sodium-reduced tantalum powder or other salt-reduced tantalum powder or reduced tantalum powder by other processes and techniques, such as electrolytic, hydrogen reduction, and the like. The starting tantalum powder can be a basic lot tantalum powder.

In addition, the present invention relates to a method for forming an article, wherein the method includes the step of additive manufacturing to form the article by utilizing the tantalum powder of the present invention to form the shape of the article or part thereof. The additive manufacturing can include or comprise laser powder bed fusion, electron beam powder bed fusion, directed energy deposition, laser cladding via a powder or wire, material jetting, sheet lamination, and/or vat photopolymerization.

It is to be understood that both the foregoing general description and the following detailed description are exemplary and explanatory only and are intended to provide further explanation of the present invention, as claimed.

BRIEF DESCRIPTION OF THE DRAWINGS

FIG. 3 is a SEM photograph of the microstructure of a sintered powder-met bar made from pressing and sintering of spherical tantalum powder of the present invention, and FIGS. 4 through 10 are SEM photographs of the microstructure of various samples of tensile bars made from additive manufacturing of spherical tantalum powder of the present invention. Compared to the sinter-bar microstructure, all printed parts have >99% density and the laser power and other print parameters were sufficiently optimized to produce complete melting of the feed powder.

DETAILED DESCRIPTION OF THE PRESENT INVENTION

Figure 1A:
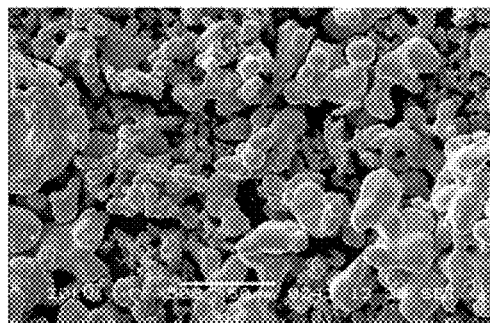
FIG. 1A is a SEM photograph of the starting basic lot tantalum powder used in Example 1 and FIG. 1B is a SEM photograph of the finished tantalum powder of Example 1 after plasma treatment.

The present invention relates to novel tantalum powders and to articles (or portions thereof) formed from the tantalum powders of the present invention. The present invention further relates to methods of making the novel tantalum powders as well as methods to form articles (or portions thereof) utilizing additive manufacturing techniques and processes.

As opposed to other spheroidization technologies, plasma spheroidization provides the energy needed to melt the tantalum quickly and produces a truly spherical powder with high purity, and/or low oxygen, and/or minimal gas entrapment and/or a controlled particle size distribution (PSD).

In more detail, the tantalum powder of the present invention comprises, consists essentially of, consists of, or includes a spherical shape wherein the powder has an average aspect ratio of from 1.0 to 1.25; a purity of tantalum of at least 99.9 wt % Ta based on total weight of the tantalum powder, excluding gas impurities; an average particle size of from about 0.5 micron to about 250 microns; a true density of from 16 g/cc to 16.6 g/cc; an apparent density of from about 4 g/cc to about 12.6 g/cc; and a Hall flow rate of 20 sec or less.

Except for the properties set forth above for the tantalum powder with respect to spherical shape, purity, average particle size, density and Hall flow rate, it is to be understood that there is no other critical limitations with regard to the type of tantalum powder, that can be used in the additive manufacturing methods of the present invention as described herein.

The tantalum powder of the present invention can be what is considered sodium reduced tantalum powder, or a reduced tantalum powder, or it can be vapor phased-reduced tantalum, or ingot-derived tantalum powder.

As indicated, the tantalum powder of the present invention has a spherical shape. This shape is defined by an average aspect ratio. The average aspect ratio of the tantalum powder or aspect ratio is defined herein as the ratio of the largest linear dimension of a particle (i.e., tantalum powder) to the smallest linear dimension of the same particle (i.e., tantalum powder) based on measuring randomly 50 particles or 100 particles or measuring randomly about 1% by weight to about 2% by weight of the batch of powder. The measuring of the tantalum particles is done using Scanning Electron Micrograph (SEM) images. True spherical particles have an aspect ratio of 1.0. For purposes of the present invention, the tantalum powder is considered spherical when the average aspect ratio is from 1.0 to 1.25, or from 1.0 to 1.2, or from 1.0 to 1.15, or from 1.0 to 1.1 or from 1.0 to 1.05, or from about 1.05 to about 1.25, or from 1.05 to about 1.2, or from 1.05 to about 1.1, or about 1.0.

The tantalum powder of the present invention is a high purity tantalum powder, meaning the tantalum powder has a purity of at least 99.9 wt % Ta, based on total weight of the tantalum powder, excluding gas impurities. The purity level can be measured by x-ray fluorescence, Inductively Coupled Plasma Atomic Emission Spectroscopy (ICP-AES) or ICP Atomic Emission Spectroscopy, or Inductively Coupled Plasma Mass Spectrometry (ICP-MS) or ICP Mass Spectrometry or Glow Discharge Mass Spectrometry (GDMS), Spark Source Mass Spec (SSMS) Analysis, or any combinations thereof. The tantalum purity can be at least 99.95 wt % Ta, at least 99.99 wt % Ta, at least 99.995 wt % Ta, or from about 99.9 wt % Ta to 99.9995 wt %, or from about 99.95 wt % Ta to 99.9995 wt % Ta, or from about 99.99 wt % Ta to 99.9995 wt % Ta or other purity values or ranges.

The tantalum powder has an average particle size of from about 0.5 micron to about 250 microns. The average particle size is determined by measuring randomly 50 particles using laser diffraction, or dynamic light scattering, or dynamic image analysis techniques, such as a HORIBA LA-960 or LA-300 Laser Particle Size Analyzer, or a HORIBA SZ-100 Nanopartica Instrument, or a HORIBA Camsizer or Camsizer X2 dynamic image analysis system. The average particle size can be from about 0.5 micron to about 10 microns, or from about 5 microns to about 25 microns, or from about 15 microns to about 45 microns, or from about 35 microns to about 75 microns, or from about 55 microns to about 150 microns, or from about 105 microns to about 250 microns.

The tantalum powder has an apparent density of from about 4 g/cc to about 12.6 g/cc, such as from about 4.5 g/cc to about 12 g/cc or from about 5 g/cc to about 10 g/cc or from about 6 g/cc to about 12.5 g/cc or other apparent density numbers within these ranges. The apparent density is measured according to ASTM B212 standard.

The tantalum powder has a Hall flow rate of 20 seconds or less. The Hall Flow test is conducted according to ASTM B213 standard, where the tantalum powder is timed as it flows through the orifice of a Hall Flowmeter funnel. The Hall flow rate of the tantalum powder of the present invention can be 19 seconds or less, 15 seconds or less, 10 seconds or less, or from 4 seconds to 20 seconds, or from 5 seconds to 20 seconds, or from 6 seconds to 20 seconds, or from 4 seconds to 15 seconds, or from 4 seconds to 12 seconds, or from 5 seconds to 15 seconds, or other values in these ranges.

The tantalum powder can be, and preferably is plasma heat-treated.

The tantalum powder can have various oxygen levels. For instance, the tantalum powder can have an oxygen level of 2,500 ppm or less, or 1,000 ppm or less, or less than 500 ppm, or less than 400 ppm, or less than 300 ppm, or less than 250 ppm, or less than 200 ppm, or less than 100 ppm, or less than 50 ppm, such as from about 20 ppm to 500 ppm, from about 40 ppm to 400 ppm, from about 50 ppm to 300 ppm, from about 100 ppm to 495 ppm, or from about 150 ppm to about 400 ppm.

As an option, the tantalum powder of the present invention can be an alloy. The alloy contains a) at least tantalum metal and b) i) one or more other metals and/or ii) non-metal elements and/or iii) metalloid elements.

As a further option, the tantalum or tantalum alloy can be doped or have one or more gaseous elements present as part of the metal or alloy and/or on the surface of the metal and/or alloy. The alloy can have a single phase. The alloy can have more than one phase.

The following one or more metals can be part of tantalum alloy powder and thus be the tantalum alloy powder of the present invention: Ti, Nb, Si, W, Mo, Re, Rh, Ta, V, Th, Zr, Hf, Cr, Mn, Sc, Y, C, B, Ni, Fe, Co, Al, Sn, Au, Th, U, Pu, and/or rare earth element(s). For instance, the tantalum powder can be a Ta—Ti alloy or a Ta—Si alloy or Ta—W alloy or Ta—Mo alloy or Ta—Nb alloy, or other Ta-metal alloys. The alloy percentages can be Ta: 30 wt % to 99.9 wt % and for the other non-Ta elements such as metals or non-metals in the alloy, the wt % can be from 0.1 wt % to 70 wt %, based on the total weight of the alloy. The Ta-metal alloy can be tantalum with one other metal, two other metals, or three or more other metals present but not as impurities. The tantalum in the Ta-metal alloy can be the predominate metal (e.g., the tantalum is the metal present in the highest percent based on the weight of the alloy). The tantalum alloy can be tantalum with one other metal or element, two other metals or elements, or three or more other metals or elements present but not as impurities.

The tantalum powder of the present invention can have one or more other properties selected from the following:
  a D10 size of from about 5 microns to about 25 microns;
  a D90 size of from about 20 microns to about 80 microns; and/or
  an oxygen content of from about 20 ppm to about 1000 ppm, such as from about 100 ppm to about 1000 ppm or from 100 ppm to about 250 ppm (based on weight of powder).

The tantalum powder of the present invention can be a non-aggregated powder, wherein the properties/parameters described herein are for a non-aggregated powder.

The tantalum powder of the present invention can be a non-agglomerated powder, wherein the properties/parameters described herein are for a non-agglomerated powder.

As an option, the tantalum powder can be phosphorous doped. For instance, the phosphorous doped levels can be at least 10 ppm, at least 50 ppm, or at least 100 ppm, or, for instance, from about 50 ppm to about 500 ppm, and the like. Phosphoric acid or ammonium hexafluorophosphate and the like are suggested as the forms of phosphorus.

As an option, the tantalum powder can be doped with other elements, such as yittrium, silica, or one or more other dopants, such as gas and/or metal dopants. The doped levels can be at least 5 ppm, at least 10 ppm, at least 25 ppm, at least 50 ppm, or at least 100 ppm, or, for instance, from about 5 ppm to about 500 ppm, and the like. One or dopants can be used for grain stabilization and/or for other property enhancements of the powder or the resulting article made from the powder.

The tantalum powder of the present invention can be used to form articles or portions thereof or parts thereof.

For instance, the article can be an orthopedic implant or other medical or dental implant. The orthopedic implant can be for a replacement of a hand, ankle, shoulder, hip, knee, bone, total joint reconstruction (arthroplasty), cranial facial reconstruction, or spinal, or other part of the human or animal body. The dental implant can be for facial reconstruction including, but not limited to, mandible or maxilla. The medical or dental implant finds usefulness in humans and other animals such as dogs, cats, and other animals.

The article can be a tracer or marker such as a medical marker, for instance, a radiographic Ta marker.

The article can be a surgical tool or part thereof. The article can be an augment.

The article can be an aerospace part.

The article can be a boss such as a boss for a coil set used in physical vapor deposition processes. The boss can comprise open cellular structures and solid structures.

The article can be any article used in metal deposition processes, such as sputtering targets, or portions thereof, or for structures used to hold sputtering targets and the like. For instance, the article can be a coil set or part thereof for physical vapor deposition processes.

The tantalum powder of the present invention can be used in spraying (e.g., cold spraying) of tantalum for coatings and/or repairs of articles or surfaces.

The tantalum powder of the present invention can be used in metal injection molding applications and processes.

The tantalum powder of the present invention can be made using a plasma heat-treating process. For instance, a process to make the tantalum powder of the present invention can comprise, consists essentially of, consists of, or include step a: plasma heat-treating a starting tantalum powder to at least partially melt at least an outer surface of the starting tantalum powder in an inert atmosphere to obtain a heat-treated tantalum powder, and then step b: cooling the heat-treated tantalum powder in an inert atmosphere to obtain said tantalum powder. The starting tantalum powder can be fully melted or at least 90% by weight melted by the plasma treatment (e.g., in the plasma torch region of the plasma reactor).

In the process, the starting tantalum powder can be a sodium-reduced tantalum powder or other reduced tantalum powder, or be any other source of tantalum powder as mentioned herein. In the process, the starting tantalum powder can be a basic lot tantalum powder.

The starting tantalum powder can be obtained by a melt reduction of potassium fluorotantalate ($K_2TaF_7$) or the starting tantalum powder can be obtained by a sodium reduction of tantalum in the vapor phase (also referred to as "vapor phase-reduced secondary particles of tantalum"). Thus, the starting tantalum powder can be produced by tantalum salt reduction.

Melt-reduced particles of tantalum can be obtained in a process involving reducing potassium fluorotantalate ($K_2TaF_7$) with sodium (or other reducing agents) in molten salt to produce tantalum particles that can be agglomerates of primary particles and then optionally water-washing, acid-washing, and drying these particles.

Vapor phase-reduced particles of tantalum can be obtained by contacting and reacting vaporized tantalum chloride with vaporized sodium. These vapor phase-reduced particles of tantalum can be composed of multiple primary particles of tantalum formed by the reaction between tantalum chloride and sodium that are encased in the sodium chloride produced by this reaction.

The starting tantalum powder used in the process to make the tantalum powder of the present invention can be what is considered basic lot powder, such as basic lot tantalum. The starting tantalum powder that can be used can be what is considered secondary particles of plasma-treated tantalum powders.

In the process, the starting tantalum powder can be ingot-derived tantalum. In the process, the starting tantalum powder can be powder metallurgy (powder-met) derived tantalum powder.

As an option, the starting tantalum powder can be non-hydrided or can be hydrided before being introduced into the plasma treatment.

In the process to make the tantalum powder, prior to step a, the starting tantalum powder can be formed by sintering a first tantalum powder to obtain a sintered powder (which can be in the form of a sintered mass such as a green log or other shape), and then e-beam melting of the sintered powder or mass to obtain an ingot, and then reducing the ingot to the starting tantalum powder. The sintering can occur at conventional sintering temperatures for tantalum powder. For instance, and only as an example, the tantalum powder can be sintered at a temperature of from about 700 deg C. to about 1,450 deg C. (or from about 800 deg C. to about 1,400 deg C., or from about 900 deg C. to about 1,300 deg C.). The sintering time can be from 1 minute to several hours, such as from about 10 minutes to 4 hours or from 10 minutes to 3 hours, or from about 15 minutes to about 2 hours or from about 20 minutes to about 1 hour or other time periods. As an option, one or more heat treatments or sinterings can occur, whether at the same temperature, same times, or at different temperatures and/or different heat treatment times. The sintering can occur in an inert atmosphere such as an argon atmosphere. The sintering can occur in a conventional furnace used for sintering of metal powders.

In the option to form a tantalum ingot that is then reduced to a powder, the tantalum ingot can have or be any volume or diameter or shape. The electron beam processing can occur at a melt rate of from about 300 lbs. to about 800 lbs. per hour using 20,000 volts to 28,000 volts and 15 amps to 40 amps, and under a vacuum of from about $1\times10^{-3}$ Torr to about $1\times10^{-6}$ Torr. More preferably, the melt rate is from about 400 lbs. to about 600 lbs. per hour using from 24,000 volts to 26,000 volts and 17 amps to 36 amps, and under a vacuum of from about $1\times10^{-4}$ Torr to $1\times10^{-5}$ Torr. With respect to the VAR processing, the melt rate is preferably of 500 lbs. to 2,000 lbs. per hour using 25 volts to 45 volts and 12,000 amps to 22,000 amps under a vacuum of $2\times10^{-1}$ Torr to $1\times10^{-4}$ Torr, and more preferably 800 lbs. to 1200 lbs. per hour at from 30 volts to 60 volts and 16,000 amps to 18,000 amps, and under a vacuum of from $2\times10^{-1}$ Torr to $1\times10^{-4}$ Torr.

The tantalum ingot can have a diameter of at least 4 inches or at least 8 inches, or have a diameter of at least 9½ inches, at least 11 inches, at least 12 inches, or higher. For instance, the tantalum ingot can have a diameter of from about 10 inches to about 20 inches or from about 9½ inches to about 13 inches, or from 10 inches to 15 inches, or from 9½ inches to 15 inches, or from 11 inches to 15 inches. The height or length of the ingot can be any amount, such as at least 5 inches or at least 10 inches or at least 20 inches, at least 30 inches, at least 40 inches, at least 45 inches, and the like. For instance, the length or height of the ingot can be from about 20 inches to about 120 inches or from about 30 inches to about 45 inches. The ingot can be cylindrical in shape, though other shapes can be used. After the formation of the ingot, optionally, the ingot can be machine cleaned using conventional techniques. For instance, the machine cleaning (off the surface) can result in a reduction in the diameter of the ingot, such as diameter reduction of from about 1% to about 10%. As a specific example, the ingot can have a nominal as-cast diameter of 12 inches and, due to machine cleaning, can have a diameter after machine cleaning of 10.75 to 11.75 inches in diameter.

The tantalum ingot can be reduced to a starting tantalum powder by making the ingot brittle and then crushing the ingot or subjecting the ingot to particle reduction steps such as milling, jaw crushing, roll crushing, cross beating and the like. To make the ingot brittle, the ingot can be hydrided such as by placing the ingot in a furnace with a hydrogen atmosphere.

With regard to the plasma heat-treating, this can also be known as plasma treatment or plasma processing. In the present invention, a RF plasma treatment or induction plasma treatment can be used. For instance, an RF thermal plasma system or an induction plasma reactor can be used, such as one from Tekna, Sherbrooke, QC, Canada, such as a PL-35LS or PL-50 or TEK-15 or other models. The central gas for the plasma can be argon, or a mixture of argon with other gases, or other gases such as helium and the like. The feed rate of the central gas can be a suitable flow such as from about 10 L/min to about 100 L/min or from about 15 L/min to about 60 L/min or other flow rates. The sheath gas for the plasma can be argon, or a mixture of argon with other gases, or other gases such as other inert gases or helium and the like. The feed rate of the sheath gas can be a suitable flow such as from about 10 L/min to about 120 L/min or from about 10 L/min to about 100 L/min or other flow rates. The carrier gas for the starting tantalum powder can be argon, or a mixture of argon with other gases (e.g., hydrogen can be added to increase the plasma intensity), or other gases such as other inert gases or helium and the like. The feed rate of the carrier gas can be a suitable flow such as from about 1 L/min to about 15 L/min or from about 2 L/min to about 10 L/min or other flow rates. The feeding rate of the starting tantalum powder into the plasma torch area can be any flow rate, such as from about 1 g/min of tantalum powder to about 120 g/min or from about 5 g/min to about 80 g/min of starting tantalum powder. Generally, a lower feed rate of the starting tantalum powder ensures more uniform and more complete spheroidal processing of the starting tantalum powder. After exiting the plasma torch area, a quench gas can be optionally used, such as through one or more quenching ports. The quench gas can be any suitable non-reactive gas, such a helium or argon. If used, the quenching gas can be fed at a variety of flow rates. For instance, the flow rate of the quench gas can be from about 25 L/min to 300 L/min or from about 50 L/min to about 200 L/min or other amounts. As an option, instead of or in addition to using a quench gas, gravity and/or a water-cooled cooling jacket can be used. The designs described in U.S. Pat. No. 5,200,595 and WO 92/19086 can be used. As an option, a passivation gas can be used after the powder is quenched or after the powder begins to cool down. The passivation gas can be oxygen, air, or a combination of air and oxygen. The flow rate of the passivation gas can be any flow rate, such as a flow rate of from about 0.1 L/min to about 1 L/min or other amounts. The chamber pressure of the plasma torch can be any suitable pressure, such as from about 0.05 MPa to about 0.15 MPa. The plate voltage can be from about 5 kV to about 7.5 kV. The frequency of the RF plasma system can be 3 MHz or other values. The plate current can be from about 2.5 A to about 4.5 A. The power can be from about 15 kW to about 35 kW. The distance from the plasma torch to the feeding nozzle or the probe position can be adjusted or varied. The distance can be 0 cm, or about 0 cm or from about 0 cm to about 8 cm. The greater the distance, the less surface evaporation of the starting powder. Thus, if the starting tantalum powder is very irregular and has aspect ratios of over 2 or over 3, an option is to have the distance of the feeding nozzle close to 0 cm. If the starting tantalum powder is more regular in shape, such as having aspect ratios of from about 1.3 to 2, the distance of the feeding nozzle can be further away from the plasma torch as an option. Also, a higher plasma powder setting can also be used to handle more irregular shaped starting tantalum powders.

As an option, the powder that has been plasma treated can be collected, such as collected under a protective atmosphere, such as an inert gas like argon. The collected powder can be passivated, such as using a water bath. The collected powder can be introduced into a water bath (e.g., submerged in a water bath).

As an option, the collected powder can be subjected to a sonication or other powder vibratory method to remove small particles such as nano materials deposited on the tantalum surface of the tantalum spheres (e.g., removing satellites and other loose material on the spheres). The resulting recovered tantalum spheres can optionally be dried, for instance, under a protective gas, such as an inert gas, like argon. This drying can be at any temperature, for instance, at a temperature of 50 deg C. to 100 deg C. for 10 mins to 24 hours, or 1 hour to 5 hours and the like. The recovered powder can be put in sealed bags such as aluminum lined anti-static bags for further use.

With the plasma treatment used in the present invention, the effort put into creating the particle size distribution of the starting tantalum powder and/or other morphology can carry through to the finished tantalum powder exiting the plasma process. Put another way, the size of the particle can be substantially maintained except for removing sharp edges and/or removing surface roughness and/or making the starting tantalum powder spherical or more spherical. Thus, prior to introducing the starting tantalum powder into the plasma treatment, the starting tantalum powder can be subjected to one or more steps to achieve desirable particle size distributions and/or other particle characteristics. For instance, the particle size distribution of the starting tantalum powder can be such that the D10 and/or D90 are within 50%, or within 40%, or within 30%, or within 25%, or within 20%, or within 15%, or within 10% or within 5% of the D50 of that starting tantalum powder.

The starting tantalum powder prior to being introduced into the plasma treatment can be subjected to one or more sieving steps or other particle screening steps, for instance to obtain a particle size distribution as described above or other sieve cuts, such as, but not limited to, a minus 200 mesh cut, a minus 225 mesh cut, a minus 250 mesh cut, a minus 275 mesh cut, a minus 300 mesh cut, and so on (with mesh being US Mesh sizes).

The starting tantalum powder, prior to plasma treating, can have one of the following particle size ranges: the average particle size can be from about 0.5 micron to about 10 microns, or from about 5 microns to about 25 microns, or from about 15 microns to about 45 microns, or from about 35 microns to about 75 microns, or from about 55 microns to about 150 microns, or from about 105 microns to about 250 microns.

In the process to make the tantalum powder, the starting tantalum powder can have a first particle size distribution, and the resulting (or finished) tantalum powder (e.g., after plasma treatment) can have a second particle size distribution, and the first particle size distribution and the second particle size distribution are within 15% of each other, within 10% of each other, or within 5% of each other, or within 2.5% of each other or within 1% of each other.

The starting tantalum powder prior to being introduced into the plasma treatment can be subjected to deoxidation treatments to remove oxygen from the tantalum powder.

The starting tantalum powder prior to plasma treating can be classified or sieved to remove various sizes, for instance, removing particles less than 20 microns, less than 15 microns, less than 10 microns, or less than 5 microns.

After exiting the plasma treatment, the plasma-treated tantalum powder can be subjected to one or more post-processing steps.

For instance, one post-processing step can be passing the plasma-treated tantalum powder through one or more sieves to remove certain sized plasma-treated tantalum powder.

For instance, one post-processing step can be sonicating or using other vibratory techniques to remove imperfections from the tantalum spheres. For instance, the tantalum spheres from the plasma treatment can be put in a water bath and sonicated to remove nano materials on the tantalum spheres and then the tantalum spheres can be recovered.

For instance, one post-processing step can be optionally subjecting the plasma-treated tantalum to at least one deoxidation or 'deox' step. The deoxidation can involve subjecting the plasma-treated tantalum to a temperature of from about 500° C. to about 1,000° C. or higher in the presence of at least one oxygen getter. For instance, the oxygen getter can be a magnesium metal or compound. The magnesium metal can be in the form of plates, pellets, or powder. Other oxygen getter material can be used.

For instance, one post-processing step can be optionally subjecting the plasma-treated tantalum to one or more heat treatment steps or annealing steps. With regard to the heat treating step of the plasma-treated tantalum, the heat treating can occur in a conventional oven under vacuum or under inert temperature. The heat treatment temperature is generally at least 800° C., or at least 1,000° C., or from about 800° C. to about 1,450° C., or from about 1,000° C. to about 1,450° C., and the like. While any heat treatment time can be used, examples include, but are not limited to, at least 10 minutes, at least 30 minutes, from about 10 minutes to about 2 hours, or more. As an option, one or more heat treatments can occur, whether at the same temperature, same times, or at different temperatures and/or different heat treatment times. After heat-treatment, if used, the plasma-treated tantalum can maintain the Hall flow rate achieved prior to the heat-treatment or be within 20% or within 10% or within 5% of that Hall flow rate.

For instance, one post-processing step can be subjecting the plasma-treated tantalum to acid leaching, such as using conventional techniques or other suitable methods. The various processes described in U.S. Pat. Nos. 6,312,642 and 5,993,513, for example, can be used herein and are incorporated in their entireties by references herein. The acid leaching can be performed using an aqueous acid solution comprising a strong mineral acid as the predominant acid, for example, nitric acid, sulfuric acid, hydrochloric acid, and the like. Also, a hydrofluoric acid (e.g., HF) in minor amounts (e.g., less than 10% by weight, or less than 5% by weight, or less than 1% by weight based on the total weight of acid) can be used. The mineral acid concentration (e.g., $HNO_3$ concentration) can range from about 20% by weight to about 75% by weight in the acid solution. The acid leach can be conducted at elevated temperatures (above room temperature to about 100° C.) or at room temperature, using acid compositions and techniques as shown, for example, in U.S. Pat. No. 6,312,642 B1. The acid leach step typically is performed under normal atmospheric conditions (e.g., approximately 760 mm Hg). The acid leach step performed using conventional acid compositions and pressure conditions, such as indicated, can remove soluble metal oxides from the deoxidized powder for those conditions.

As an option, the plasma-treated tantalum can be nitrogen doped. With respect to nitrogen, the nitrogen can be in any state, such as a gas, liquid, or solid. The powders of the present invention, can have any amount of nitrogen present as a dopant or otherwise present. Nitrogen can be present as a crystalline form and/or solid solution form at any ratio. Nitrogen doped levels can be from 5 ppm to 5,000 ppm nitrogen or higher.

The plasma-treated tantalum of the present invention can be used in a number of ways. For instance, the plasma-treated tantalum can be used in additive manufacturing or processing which is sometimes referred to as 3-D printing to form an article or part of an article. The plasma-treated tantalum powder of the present invention can be used in processes or devices that permit the use of metal powders. With the plasma-treated powder of the present invention, the ease of conducting additive manufacturing is achieved. In addition or alternatively, with the plasma-treated powder of the present invention, the feed of the powder to the additive manufacturing devices is improved and/or the resulting article is more accurately obtained from the design programmed into the printing device.

The additive processes that can utilize the plasma-treated tantalum powder of the present invention include laser powder bed fusion, electron beam powder bed fusion, directed energy deposition, laser cladding via a powder or wire, material jetting, sheet lamination, or vat photopolymerization.

Some of these additive processes are referred to as laser metal fusion, laser sintering, metal laser melting, or direct metal printing, or direct metal laser sintering. In this process, a high power laser beam is scanned over a bed of powder, sintering the powder in the required shape, in the path of the laser beam. After each layer, the bed is lowered by a short distance and a new layer of powder applied. The entire process runs in a sealed chamber with a controlled gas atmosphere which is either inert (e.g. argon) or active to fine-tune material/product properties.

Some of these additive processes are referred to as laser metal deposition (LIVID) or near net shape. In this process, a high-power laser beam is used, connected to a robot or gantry system, to form a melt pool on a metallic substrate into which powder or metal wire is fed. In LIVID, the powder is contained in a carrier gas and directed to the substrate through a nozzle that is concentric with the laser beam. Alternatively, a wire can be fed from the side. The powder or wire is melted to form a deposit that is bonded to the substrate and grown layer-by-layer. An additional gas jet, concentric with the laser beam, can provide additional shield or process gas protection.

Some of these additive processes are referred to as gas-metal arc welding and plasma welding techniques to melt the metal powder to form a 3D shape layer by layer. In this process, metal wire is added as the electrode melts in the arc and its droplets form layers on the substrate. Processes with lower heat input, such as controlled short-circuit metal transfer, are preferred given the heat sensitivity of most materials used in additive manufacturing. Shielding gases protect the layers against ambient air.

Plasma additive manufacturing is similar to laser metal deposition, where powder is guided towards the substrate in a gas stream and fused by the plasma heat.

Some of these additive processes are referred to as thermal spraying. In this process, molten, heated powder particles or droplets from molten wires are accelerated in a gas stream towards the substrate, where local adherence is ensured by kinetic energy and heat. When used for additive manufacturing, thermal spraying is applied layer-by-layer to build up components without geometrical complexity, e.g. tubes or reducers. Process gases protect the hot material against ambient atmospheric gases and help to fine-tune material properties.

Some of these additive processes are referred to as electron beam melting or a powder bed fusion process using an electron beam in a vacuum. This process is similar to laser sintering.

The additive manufacturing device or process used to form the articles can have one or more of the following settings: a laser power of from 150 W to about 175 W or from 155 W to 165 W; a scan speed of from about 100 mm/s to about 500 mm/s, such as from about 300 mm/s to about 400 mm/s; hatch spacing of from about 30 microns to about 100 microns, such as from about 80 microns to about 90 microns; a layer thickness of from about 10 microns to about 50 microns, such as from about 30 microns to about 40 microns; and/or an energy density of from about 3 $J/mm^2$ to about 20 $J/mm^2$, such as from about 4 $J/mm^2$ to about 6 $J/mm^2$. Sometimes, a lower than maximum laser setting can be utilized so as to reduce thermal input and/or minimize thermal stress and/or minimize part deformation.

For additive manufacturing, preferably a tantalum baseplate is utilized but other base plates such as stainless steel or stainless steel alloys can be used. Tantalum baseplates can minimize the difference of Coefficient of Thermal Expansion (CTE) and/or the difference in thermal conductivities between the part and base plant. The effect can minimize thermal residual stresses in the part and/or can prevent lift-up of the part from the plate.

With the tantalum powder of the present invention and utilizing additive manufacturing processes, it was discovered that desirable tensile properties of the resulting article formed from the tantalum powder of the present invention can be achieved. One or more of these properties can be enhanced if the article is annealed such as at a temperature of from about 800 deg C. to about 2,000 deg C. (for instance for 10 mins to 10 hours, or from 30 minutes to 3 hours, or from 1 hour to 2 hours).

One or more of the following properties can be achieved with the present invention in forming additive manufactured (AM) objects or articles. Ultimate tensile strength (UTS) can be at least 50% or at least 100% greater than wrought Ta of the same shape. The UTS can be over 50 KSI, over 70 KSI, over 80 KSI, or over 90 KSI, such as from about 50 KSI to about 100 KSI. The Yield Stress can be at least 50% or at least 100% greater than wrought Ta of the same shape. The Yield Stress can be over 35 KSI, over 40 KSI, over 50 KSI, or over 80 KSI, such as from about 35 KSI to about 90 KSI. An annealed AM article of the present invention showed improved Yield Stress. An annealed AM article of the present invention showed improved Yield Stress without compromising the UTS. Elongation can be from about 1% to about 50%, such as from about 3 to 40% or from 5% to 35%. An annealed AM article of the present invention showed improved elongation. With the present invention, a balance of acceptable and/or good UTS, Yield and Elongation are possible.

With the plasma-treated tantalum powder utilized in additive manufacturing, various articles are possible and the quality and accuracy of the article can be excellent. For instance, the article can be an orthopedic implant or other medical or dental implant. The orthopedic implant can be for a replacement of a hand, ankle, shoulder, hip, knee, bone, total joint reconstruction (arthroplasty), cranial facial reconstruction, or spinal, or other part of the human or animal body. The dental implant can be for facial reconstruction including, but not limited to, mandible or maxilla. The medical or dental implant finds usefulness in humans and other animals such as dogs or cats.

The article can be a boss such as a boss for a coil set used in physical vapor deposition processes. The boss can comprise open cellular structures and solid structures.

The article can be any article used in metal deposition processes, such as sputtering targets, or portions thereof, or for structures used to hold sputtering targets and the like. For instance, the article can be a coil set or part thereof for physical vapor deposition processes.

As an option, the plasma-treated tantalum can be further processed to form a capacitor electrode (e.g., capacitor anode). This can be done, for example, by compressing the plasma treated powder to form a body, sintering the body to form a porous body, and anodizing the porous body. The pressing of the powder can be achieved by any conventional techniques such as placing the powder in a mold and subjecting the powder to a compression by use of a press, for instance, to form a pressed body or green body. Various press densities can be used, and include, but are not limited to, from about 1.0 g/cm$^3$ to about 7.5 g/cm$^3$. The powder can be sintered, anodized, and/or impregnated with an electrolyte in any conventional manner. For instance, the sintering, anodizing, and impregnation techniques described in U.S. Pat. Nos. 6,870,727; 6,849,292; 6,813,140; 6,699,767; 6,643,121; 4,945,452; 6,896,782; 6,804,109; 5,837,121; 5,935,408; 6,072,694; 6,136,176; 6,162,345; and 6,191,013 can be used herein and these patents are incorporated in their entirety by reference herein. The sintered anode pellet can be, for example, deoxidized in a process similar to that described above for the powder. The anodized porous body further can be impregnated with manganese nitrate solution, and calcined to form a manganese oxide film thereon. Wet valve metal capacitors can use a liquid electrolyte as a cathode in conjunction with their casing. The application of the cathode plate can be provided by pyrolysis of manganese nitrate into manganese dioxide. The pellet can be, for example, dipped into an aqueous solution of manganese nitrate, and then baked in an oven at approximately 250° C. or other suitable temperatures to produce the manganese dioxide coat. This process can be repeated several times through varying specific gravities of nitrate to build up a thick coat over all internal and external surfaces of the pellet. The pellet optionally can be then dipped into graphite and silver to provide an enhanced connection to the manganese dioxide cathode plate. Electrical contact can be established, for example, by deposition of carbon onto the surface of the cathode. The carbon can then be coated with a conductive material to facilitate connection to an external cathode termination. From this point the packaging of the capacitor can be carried out in a conventional manner, and can include, for example, chip manufacture, resin encapsulation, molding, leads, and so forth.

As part of forming an anode, for example, a binder, such as camphor ($C_{10}H_{16}O$) and the like, can be added to the powder, for instance, in the amount of 3-5 wt % based on 100 wt % of the powder and the mixture can be charged into a form, compression-molded, and sintered by heating for 0.3-1 hour at 1,000-1,400° C. while still in a compressed state. Such a molding method makes it possible to obtain pellets consisting of sintered porous bodies.

When a pellet obtained using the above-described molding process is employed as a capacitor anode, before the powder is compression-molded, it is preferable to embed lead wires into the powder in order to integrate the lead wires into the pellet.

The capacitor can be manufactured using the above-described pellet. A capacitor equipped with an anode can be obtained by oxidizing the surface of the pellet, a cathode facing the anode, and a solid electrolyte layer disposed between the anode and cathode.

A cathode terminal is connected to the cathode by soldering and the like. In addition, an exterior resin shell is formed around a member composed of the anode, cathode, and solid electrolyte layer. Examples of materials used to form the cathode include graphite, silver, and the like. Examples of materials used to form the solid electrolyte layer include manganese dioxide, lead oxide, electrically conductive polymers, and the like.

When oxidizing the surface of a pellet, for example, a method can be used that involves treating the pellet for 1-3 hours in an electrolyte solution such as nitric acid, phosphoric acid and the like with a concentration of 0.1 wt % at a temperature of 30-90° C. by increasing the voltage to 20-60V at a current density of 40-120 mA/g. A dielectric oxide film is formed in the portion oxidized at such time.

As indicated, the plasma-treated tantalum of the present invention can be used to form a capacitor anode (e.g., wet anode or solid anode). The capacitor anode and capacitor (wet electrolytic capacitor, solid state capacitor, etc.) can be formed by any method and/or have one or more of the components/designs, for example, as described in U.S. Pat. Nos. 6,870,727; 6,813,140; 6,699,757; 7,190,571; 7,172, 985; 6,804,109; 6,788,523; 6,527,937 B2; 6,462,934 B2; 6,420,043 B1; 6,375,704 B1; 6,338,816 B1; 6,322,912 B1; 6,616,623; 6,051,044; 5,580,367; 5,448,447; 5,412,533; 5,306,462; 5,245,514; 5,217,526; 5,211,741; 4,805,704; and 4,940,490, all of which are incorporated herein in their entireties by reference. The powder can be formed into a green body and sintered to form a sintered compact body, and the sintered compact body can be anodized using conventional techniques. It is believed that capacitor anodes made from the powder produced according to the present invention have improved electrical leakage characteristics. The capacitors of the present invention can be used in a variety of end uses such as automotive electronics; cellular phones; smart phones; computers, such as monitors, mother boards, and the like; consumer electronics including TVs and CRTs; printers/copiers; power supplies; modems; computer notebooks; and disk drives.

Further details of the starting tantalum powder, the plasma-treated tantalum powder, and components formed from the tantalum powder are provided below and further form optional aspects of the present invention.

With the methods of the present invention, the tantalum powder can be made that can have:
- a) an apparent density of from about 4 g/cc to about 12.3 g/cc,
- b) a D10 particle size of from about 5 microns to about 25 microns,
- c) a D50 particle size of from about 20 microns to about 50 microns,
- d) a D90 particle size of from about 30 microns to about 100 microns, and/or
- e) a BET surface area of from about 0.05 $m^2/g$ to about 20 $m^2/g$.

The tantalum powder can have at least one of the following properties:
- a) an apparent density of from about 9 g/cc to about 12.3 g/cc,
- b) a D10 particle size of from about 12 microns to about 25 microns,
- c) a D50 particle size of from about 20 microns to about 40 microns,
- d) a D90 particle size of from about 30 microns to about 70 microns, and/or
- e) a BET surface area of from about 0.1 $m^2/g$ to about 15 $m^2/g$.

For purposes of the present invention, at least one of these properties, at least two, at least three, at least four, or all five properties can be present.

In at least one embodiment of the present invention, the plasma-treated tantalum powder (or starting tantalum powder) or any article formed with the tantalum powder of the present invention, can have the following characteristics, but it is to be understood that the powder or article can have characteristics outside of these ranges:

Purity levels:
Oxygen content of from about 20 ppm to about 60,000 ppm or about 100 ppm to about 60,000 ppm, such as from about 20 ppm to 1,000 ppm, or from about 40 ppm to about 500 ppm or from about 50 ppm to about 200 ppm, or from about 250 ppm to about 50,000 ppm, or from about 500 ppm to about 30,000 ppm, or from about 1000 ppm to about 20,000 ppm oxygen. An oxygen (in ppm) to BET (in $m^2/g$) ratio can be from about 2,000 to about 4,000, such as from about 2,200 to about 3,800, from about 2,400 to about 3,600, from about 2,600 to about 3,400, or from about 2,800 to about 3,200, and the like.

A carbon content of from about 1 ppm to about 100 ppm and more preferably, from about 10 ppm to about 50 ppm or from about 20 ppm to about 30 ppm carbon.

A nitrogen content of from about 5 ppm to about 20,000 ppm, or from about 100 ppm to about 20,000 ppm or higher and more preferably from about 1,000 ppm to about 5,000 ppm or from about 3,000 ppm to about 4,000 ppm or from about 3,000 ppm to about 3,500 ppm nitrogen.

A hydrogen content of from about 1 ppm to about 1,000 ppm, from about 10 ppm to about 1,000 ppm, and more preferably from about 300 ppm to about 750 ppm, or from about 400 ppm to about 600 ppm hydrogen.

An iron content of from about 1 ppm to about 50 ppm, and more preferably from about 5 ppm to about 20 ppm iron.

A nickel content of from about 1 ppm to about 150 ppm, and more preferably from about 5 ppm to about 100 ppm or from about 25 ppm to about 75 ppm nickel.

A chromium content of from about 1 ppm to about 100 ppm and more preferably from about 5 ppm to about 50 ppm or from about 5 ppm to about 20 ppm chromium.

A sodium content of from about 0.1 ppm to about 50 ppm and more preferably from about 0.5 ppm to about 5 ppm sodium.

A potassium content of from about 0.1 ppm to about 100 ppm and more preferably from about 5 ppm to about 50 ppm, or from about 30 ppm to about 50 ppm potassium.

A magnesium content of from about 1 ppm to about 50 ppm and more preferably from about 5 ppm to about 25 ppm magnesium.

A phosphorus (P) content of from about 1 ppm to about 500 ppm, or from about 5 ppm to about 500 ppm and more preferably from about 100 ppm to about 300 ppm phosphorus.

A fluoride (F) content of from about 1 ppm to about 500 ppm and more preferably from about 25 ppm to about 300 ppm, or from about 50 ppm to about 300 ppm, or from about 100 ppm to about 300 ppm.

The plasma treated powder (or starting tantalum powder) (primary, secondary, or tertiary) can have a particle size distribution (based on overall %) as follows, based on mesh size:
- +60 # of from about 0.0 to about 1% and preferably from about 0.0 to about 0.5% and more preferably 0.0 or about 0.0.
- 60/170 of from about 45% to about 70% and preferably from about 55% to about 65%, or from about 60% to about 65%.
- 170/325 of from about 20% to about 50% and preferably from about 25% to about 40% or from about 30% to about 35%.
- 325/400 of from about 1.0% to about 10% and preferably from about 2.5% to about 7.5% such as from about 4 to about 6%.
- −400 of from about 0.1 to about 2.0% and preferably from about 0.5% to about 1.5%.

The powder, when formed in to an anode with a sintering temperature of 1150° C. for 10 minutes with a formation temperature of 60° C. and a press density of 4.5 g/cc and a formation voltage of 6 V has a capacitance of from about 20,000 CV/g to about 800,000 CV/g, such as from about 100,000 CV/g to about 300,000 CV/g, or from about 150,000 CV/g to about 400,000 CV/g. Also, the leakage current can be less than 20 nA/μFV and can be from about 2.5 to about 15 nA/μFV or from about 3.0 to about 10 nA/μFV. The values or ranges for capacitance and/or leakage current are also possible with a sintering temperature of 1200° C. or 1250° C. for 10 minutes and/or a formation voltage of from 5 volts to 16 volts. Also, any individual value within the ranges for capacitance and leakage current can be used for purposes of the present invention.

The plasma-treated tantalum powder of the present invention can also have a pore size distribution which can be unimodal or multi-modal, such as bi-modal.

The plasma-treated tantalum powders of the present invention can have a BET surface area of from about 0.01 $m^2/g$ to about 20 $m^2/g$, and more preferably from about 0.05 $m^2/g$ to about 5 $m^2/g$ such as from about 0.1 $m^2/g$ to about 0.5 $m^2/g$.

As discussed earlier, the starting tantalum powder can be obtained from a variety of processes used to obtain the tantalum powder. As stated, the starting tantalum powder to be plasma-treated can be raw tantalum powder. Raw tantalum powder (e.g., basic lot powder) can be obtained or produced by processes which are capable of providing powders having a surface area of at least 0.1 $m^2/g$ or at least 0.5 $m^2/g$. Any tantalum powders can be used in this regard. Specific examples of the raw tantalum production process include sodium/halide flame encapsulation (SFE), a sodium reduction process of potassium fluorotantalate, a magnesium reduction process of a tantalum oxide, a gas-phase hydrogen reduction process of tantalum pentachloride, and a pulverizing process of tantalum metal. In the SFE process, vapor-phase sodium reacts with a gaseous metal halide, such as gaseous tantalum halide, to produce an aerosol core material and salt. Techniques employed for the SFE process which can be adapted for preparation of raw tantalum powder for the present invention are described in U.S. Pat. Nos. 5,498,446 and 7,442,227, which are incorporated in their entireties by reference herein. See, also, Barr, J. L. et al., "Processing salt-encapsulated tantalum nanoparticles for high purity, ultra high surface area applications," J. Nanoparticle Res. (2006), 8:11-22. An example of the chemistry employed for the production of metal powder by the SFE process of the '446 patent is as follows, wherein "M" refers to a metal such as Ta: $MCl_x + XNa + Inert \rightarrow M + XNaCl + Inert$. Tantalum pentachloride is an example of a tantalum halide that can be used as the reactant $MCl_x$, and argon gas may be used as the Inert and carrying gas, in this chemistry. Initially, core particles (e.g., Ta) are produced at the flame and grow by coagulation while the salt remains in the vapor phase. The salt condenses onto the core particles with heat loss, and uncoated core particles are scavenged by the salt particles as salt-encapsulated particles grow. The salt encapsulate allows for size and morphology control and can protect the core particles, such as from oxidation and/or hydrolysis, during storage and handling before use in plasma-treated tantalum powder production. The encapsulate can be removed in known manners, such as vacuum sublimation and/or a water wash, before use of the tantalum powders in plasma-treated tantalum powder production.

The starting tantalum powder alternatively can be obtained by the sodium reduction of tantalum salt, such as sodium tantalate fluoride in diluent salt, or other chemical or ingot processing methods.

The raw or starting tantalum powder may comprise primary particles that have an average size in the range of 1 nm to about 500 nm, or 10 nm to 300 nm, or 15 nm to 175 nm, or 20 nm to 150 nm, or 25 nm to 100 nm, or 30 nm to 90 nm, or other sizes. The average size and distribution of the primary particle sizes can depend on the method of preparation. The primary particles may tend to form clusters or agglomerates of larger size than the primary particles. The shapes of raw or starting tantalum powder particles may include, but are not limited to, flaked, angular, nodular, or spherical, and any combinations thereof or variations thereof. The raw powder used to practice the present invention can have any purity with respect to the tantalum metal with higher purities being preferred. For instance, the tantalum purity (e.g., by wt %) of the raw or starting powder can be 95% Ta or greater, or 99% Ta or greater such as from about 99.5% Ta or greater and more preferably 99.95% Ta or greater and even more preferably 99.99% Ta or greater, or 99.995% Ta or greater or 99.999% Ta or greater.

At any stage, before or after plasma-treatment, the tantalum powder can be passivated using an oxygen-containing gas, such as air, as part of the plasma-treated tantalum powder production process of the present invention. Passivation typically is used to form a stabilizing oxide film on the powder during processing and in advance of sintered body formation using the powder. A powder production process of the present invention therefore can include hydrogen doping and passivating operations.

Passivating the tantalum powder can be by any suitable method. Passivation can be achieved in any suitable container, for example, in a retort, a furnace, a vacuum chamber, or a vacuum furnace. Passivation can be achieved in any of the equipment used in processing, such as heat treating, deoxidizing, nitriding, delubing, granulating, milling, and/or sintering, the metal powder. The passivating of the metal powder can be achieved under vacuum. Passivation can include backfilling of the container with an oxygen containing gas to a specified gas pressure, and holding the gas in the container for a specified time. The oxygen content level of the gas used in powder passivation can be from 1 to 100 wt % oxygen, or from 1 to 90 wt %, or from 1 to 75 wt %, or from 1 to 50 wt %, or from 1 to 30 wt %, or from 20 to 30 wt %, or an oxygen content that is the same as or greater than that of air or atmospheric air, or other content levels. The oxygen can be used in combination with an inert gas, such as nitrogen, argon, or combinations of these, or other inert gases. The inert gas does not react with the tantalum during the passivation process. The inert gas, such as nitrogen gas and/or argon gas, preferably can compose all or essentially all (e.g., >98%) of the remaining portion of the passivating gas other than the oxygen. Air can be used as the passivating gas. Air can refer to atmospheric air or dry air. The composition of dry air typically is nitrogen (about 75.5 wt %), oxygen (about 23.2 wt %), argon (about 1.3 wt %), and the rest in a total amount of less than about 0.05%. The content level of hydrogen in dry air is about 0.00005 vol %.

Additional techniques that may be employed for the passivation process can be adapted from those disclosed in U.S. Pat. No. 7,803,235, which is incorporated in its entirety by reference herein.

The salt-containing tantalum can be any salt capable of having tantalum contained therein such as a potassium-fluoride tantalum. With respect to the agent capable of reducing the salt to tantalum and a second salt in the reaction container, the agent which is capable of doing this reduction is any agent which has the ability to result in reducing the salt-containing tantalum to just tantalum metal and other ingredients (e.g. salt(s)) which can be separated from the tantalum metal, for example, by dissolving the salts with water or other aqueous sources. Preferably, this agent is sodium. Other examples include, but are not limited to, lithium, magnesium, calcium, potassium, carbon, carbon monoxide, ionic hydrogen, and the like. Typically, the second salt which also is formed during the reduction of the salt-containing tantalum is sodium fluoride. Details of the reduction process which can be applied to the present invention in view of the present application are set forth in Kirk-Othmer, Encyclopedia of Chemical Technology, $3^{rd}$ Edition, Vol 22, pp. 541-564, U.S. Pat. Nos. 2,950,185; 3,829,310; 4,149,876; and 3,767,456. Further details of the processing of tantalum can be found in U.S. Pat. Nos. 5,234,491; 5,242,481; and 4,684,399. All of these patents and publications are incorporated in their entirety by reference herein.

The above-described process can be included in a multi-step process which can begin with low purity tantalum, such as ore-containing tantalum. One of the impurities that can be substantially present with the tantalum is niobium. Other impurities at this stage are tungsten, silicon, calcium, iron, manganese, etc. In more detail, low purity tantalum can be purified by mixing the low purity tantalum which has tantalum and impurities with an acid solution. The low purity tantalum, if present as an ore, should first be crushed before being combined with an acid solution. The acid solution should be capable of dissolving substantially all of the tantalum and impurities, especially when the mixing is occurring at high temperatures.

Once the acid solution has had sufficient time to dissolve substantially, if not all, of the solids containing the tantalum and impurities, a liquid solid separation can occur which will generally remove any of the undissolved impurities. The solution is further purified by liquid-liquid extraction. Methyl isobutyl ketone (MIBK) can be used to contact the tantalum rich solution, and deionized water can be added to create a tantalum fraction. Then, with the liquid containing at least tantalum, the liquid is permitted to crystallize into a salt with the use of vats. Typically, this salt will be a potassium tantalum fluoride salt. More preferably, this salt is $K_2TaF_7$. This salt is then reacted with an agent capable of reducing the salt into 1) tantalum and 2) a second salt as described above. This compound will typically be pure sodium and the reaction will occur in a reaction container described above. As stated above, the second salt byproducts can be separated from the tantalum by dissolving the salt in an aqueous source and washing away the dissolved salt.

The present invention will be further clarified by the following examples, which are intended to be purely exemplary of the present invention.

EXAMPLES

Example 1

Commercially available $KTa_2F_7$ (KTAF) and sodium were used to obtain tantalum powder using a sodium reduction of the KTAF utilizing standard industry processes. The salt byproducts were removed by washing and acid leaching and drying steps. The resulting tantalum powder had a BET of about 0.1 $m^2/g$. This tantalum was a basic lot tantalum powder. FIG. 1A shows a SEM of this starting tantalum powder. The starting tantalum powder was divided into three lots of powder—Lots A, B, and C and each was separately plasma treated as described below.

Next, the basic lot tantalum powder was plasma treated. Particularly, the basic lot tantalum powder was spheroidized by introducing the basic lot tantalum powder into a feeder. The feeder had an argon supply (5 LPM) that aerosolizes the powder into the plasma spheroidization reactor (TEK15, from Tekna, Canada). The feed rate of the powder was maintained at 0.75 kg/hr by adjusting the feeder. The aerosolized powder was introduced into the plasma heat source of the plasma reactor. The plasma reactor had an induction plasma torch using a design described in U.S. Pat. No. 5,200,595 and WO 92/19086 using concentric tubes. The plasma energy used to spheroidize the powder was 15 KW with plate voltage set at 6.5 V, plate current set at 2.3 A and grid current set at 0.4 A. The reactor was inerted using argon gas flow with carrier gas flow set at 5 LPM, sheath gas flow set at 30 LPM, central gas flow set at 10 LPM and nozzle gas flow set at 1 LPM. The plasma intensity was increased by adding hydrogen gas (using flow rates of 4 LPM). The run conditions are summarized in Table 1. The basic lot tantalum powder introduced into the plasma torch was at least partially melted and then spheroidized, and the liquid drops of tantalum were carried downstream from the plasma torch where they cooled rapidly by an active water cooling jacket on the plasma reactor. In this example, the cooled spheroid tantalum powder dropped to the bottom of the plasma reactor via gravity and the spheroid powder was collected under argon gas blanket, and passivated in a water bath. Once under water, the slurry was sonicated (energy <150 W/gal.) to remove potential nanomaterials deposited on surface of spheroid powder. The washed tantalum spheres were then dried under argon at 80° C. for 4 hours. The dried powder was then packaged in Al lined anti-static bags until tested for propertites.

Figure 1B:
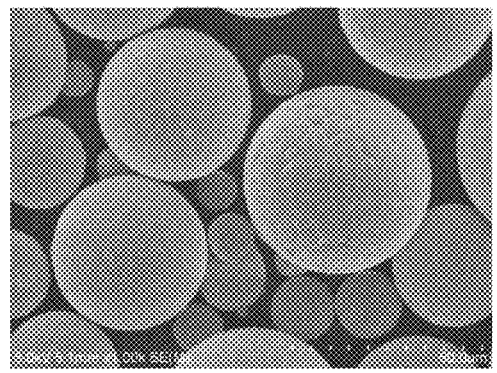

The results are shown in Table 2 for the impurity levels, and in Table 3 for the particle size distribution, and the apparent density and Hall flow rate and FIG. 1B shows a SEM image of the plasma treated powder of Lot A. In each of Lots A, B, and C, the aspect ratio was about 1.0 to 1.1.

TABLE 1

| Feed | Power | Argon gas pressure | Argon Flow - LPM | | | | Hydrogen (LPM) | Plate Voltage (V) | Plate Current (A) | Grid Current (A) | Ta feed rate (kg/hr) |
| --- | --- | --- | --- | --- | --- | --- | --- | --- | --- | --- | --- |
| | | | Carrier Gas | Shealth Gas | Central Gas | Nozzle | | | | | |
| Tantalum | 15 KW | 15 psia | 5 | 30 | 10 | 1 | 4 | 6.55 | 2.3 | 0.4 | 0.75 |

TABLE 2

| Lot | (ppm) | | | | | | | | | | | | |
| --- | --- | --- | --- | --- | --- | --- | --- | --- | --- | --- | --- | --- | --- |
| | O | N | H | C | S | Cr | Fe | Mg | K | Ni | Na | Ti | W |
| A | 310 | 22 | 71 | 11 | <10 | <2 | <3 | <1 | 2 | 25 | 2 | <1 | <1 |
| B | 276 | 40 | 65 | 10 | <10 | <2 | <3 | <1 | 2 | 12 | <1 | <1 | <1 |
| C | 354 | 18 | 70 | 14 | <10 | <2 | <3 | <1 | <1 | 11 | <1 | <1 | <1 |

TABLE 3

| | (microns) | | | Apparent | Hall Flow |
|---|---|---|---|---|---|
| Lot | D10 | D50 | D90 | Density | (s) |
| A | 16.40 | 34.23 | 65.17 | 9.78 | 5.97 |
| B | 20.46 | 39.87 | 71.33 | 9.75 | 5.85 |
| C | 24.38 | 44.06 | 76.44 | 9.58 | 6.34 |

Example 2

Figure 2A:
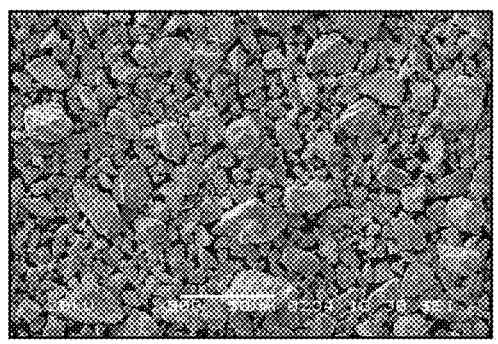
FIG. 2A is a SEM photograph of the starting basic lot tantalum powder used in Example 2 (after being crushed and sieved) and FIG. 2B is a SEM photograph of the finished tantalum powder of Example 2 after plasma treatment.

In this example, basic lot tantalum powder (sodium reduced powder) as in Example 1 was used. This basic lot tantalum powder had a BET of 0.1 $m^2/g$. The basic lot tantalum powder was pressed and sintered into green logs utilizing a sinter temperature of about 1,000 deg C. for one hour. The green logs were fed into an e-beam furnace where the metal was melted via a crucible. The melt was drawn through a die where the tantalum solidified and formed the ingot. The tantalum ingot was hydrided using a high temperature furnace with a hydrogen atmosphere and allowed to cool to room temperature after hydriding. The hydrided ingot was then crushed (using a jaw crush and then a roll crush) and screened to a sieve side of −20 #. The crushed ingot was screened to a desired size cut which was 10-25 microns for Lot A (or 35-75 microns for Lot B). The screened powder for each Lot was then acid leached. The powder was then subjected to deoxidation using magnesium to lower the oxygen levels to below 500 ppm. FIG. 2A shows a SEM of this starting tantalum powder. Each of Lot A and Lot B was then separately subjected to plasma treating in the same manner as Example 1.

Figure 2B:
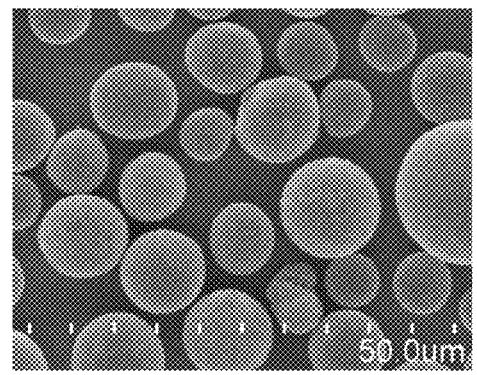

The results are shown in Table 4 for the impurity levels, and in Table 5 for the particle size distribution, and the apparent density and Hall flow rate and FIG. 2B shows a SEM image of the plasma treated powder of Lot A. In each of Lots A and B, the aspect ratio was about 1.0 to 1.1.

TABLE 4

| | (ppm) | | | | | | | | | | | | |
|---|---|---|---|---|---|---|---|---|---|---|---|---|---|
| Lot | O | N | H | C | S | Cr | Fe | Mg | K | Ni | Na | Ti | W |
| A | 633 | 12 | 415 | 15 | <10 | <2 | <3 | <1 | <1 | 20 | 1 | <1 | <1 |
| B | 936 | 54 | 1986 | 21 | <10 | <2 | <3 | <1 | <1 | 10 | 2 | 4 | <1 |

TABLE 5

| | (microns) | | | Apparent | Hall Flow |
|---|---|---|---|---|---|
| Lot | D10 | D50 | D90 | Density | (s) |
| A | 7 | 13 | 21 | 9.3 | 7.3 |
| B | 20 | 40 | 71 | 9.5 | 9.8 |

Example 3

The tantalum powder of Example 2 was used in a 3D printing or additive manufacturing process. Specifically, tantalum builds were performed on a Trumpf TruPrint 1000 with a build volume of Dia. 100×100 mm and maximum laser power of 175 W. The base plate used was Type 316 austenitic chromium nickel stainless steel.

In the experiment, the spheroidized tantalum powder of Example 2 was sufficient for Laser Powder Bed (L-PBF) printing and fully dense tensile bars and demonstration parts, with alternating solid and mesh aspects and remarkable overhang, were produced. Specifically, tensile bars were printed with 1 mm oversize to standard dimensions (ASTM E8). The bars were machined to final dimensions on a lathe. Tensile properties were measured on an Instron 4210 Tensile Tester. Tensile bars were analyzed for microstructure and hardness. For microstructure analysis, the samples were mounted in epoxy, cut with a diamond saw. The mounted sample was polished and etched in acid and the grains were characterized on a Unition Versamet 2 metallographic microscope. Microhardness was tested using a LECO LM700-AT Tester with AMH32 Software.

The printing parameters and laser parameters used were the preferred parameters mentioned above. The results included a >99.5% density with good overhang in the test build. A cube (25 mm×25 mm×25 mm) with alternating open mesh and solid portions was printed as well in this experiment and this demonstration part showed high resolution (<30 um) of features with the ability to successfully print open cellular structures. This alternating mesh-solid structure is often required for lightweight additively manufactured aerospace components and industrial parts, as well as for medical implants to allow improved osteointegration.

Compared to wrought tantalum, the present invention's tensile bars showed high yield strength (YS) and slightly lower elongation. Elongation properties were improved after annealing without decreasing YS.

Example 4

In this example, basic lot tantalum powder (sodium reduced powder) as in Example 1 was used. This basic lot tantalum powder had a BET of 0.1 $m^2/g$. The basic lot tantalum powder was pressed and sintered into green logs utilizing a sinter temperature 2500 deg C. to 3000 deg C. for three hours. The green logs were fed into an e-beam furnace where the metal was melted via a crucible. The melt was drawn through a die where the tantalum solidified and formed the ingot. The tantalum ingot was hydrided using a high temperature furnace with a hydrogen atmosphere and allowed to cool to room temperature after hydriding. The hydrided ingot was then crushed (using a jaw crush and then a roll crush) and screened to a sieve side of −20 #. The crushed ingot was screened to a desired size cut which was 10-25 microns for Lot A2 and D2, or 15-40 microns for Lot E2 and F2 or 35-105 microns for Lot B2, C2. The screened powder for each Lot was then acid leached. The powder in each Lot was then subjected to deoxidation using magnesium chips (700 deg C. for 2 hours) to lower the oxygen levels to various levels, all below 1000 ppm, as shown in Table 6. Standard (A2, D2) and low (B2, E2) oxygen impurity powders were produced. Each of Lot A2 through F2 was then separately subjected to plasma treating in the same manner as Example 1. For Lot C2 and F2, besides the initial deoxidation as for Lot B2 and E2, an additional deoxidation (with magnesium chips for 2 hours at 700 deg C.) was conducted after spheroidization (a double deoxidation) to achieve ultra low oxygen impurity powders (Lot C2, F2). The difference in oxygen amounts for A2, D2, B2, and E2 is due to the particle size distribution of each Lot as shown in Table 7.

The results are shown in Table 6 for the impurity levels, and Table 7 for the particle size distribution, and the apparent density and Hall flow rate. In each of Lots A2 through F2, the aspect ratio was about 1.0 to 1.1.

TABLE 6

| Lot | (ppm) | | | | | | | | | | | | |
|---|---|---|---|---|---|---|---|---|---|---|---|---|---|
| | O | N | H | C | S | Cr | Fe | Mg | K | Ni | Na | Ti | W |
| A2 | 633 | 12 | 415 | 15 | <10 | <2 | <3 | <1 | <1 | 20 | 1 | <1 | <1 |
| B2 | 171 | 11 | 52 | 8 | <10 | <2 | <3 | <1 | 1 | <1 | <1 | <1 | <1 |
| C2 | 49 | 19 | 7 | 12 | <10 | <2 | 4 | 1 | <1 | <1 | <1 | <1 | <1 |
| D2 | 936 | 54 | 1986 | 21 | <10 | <2 | <3 | <1 | <1 | 10 | 2 | 4 | <1 |
| E2 | 356 | 16 | 118 | 7 | <10 | <2 | 4 | <1 | <1 | 2 | <1 | <1 | <1 |
| F2 | 87 | 19 | 8 | 8 | <10 | <2 | 4 | 1 | <1 | <1 | <1 | <1 | <1 |

TABLE 7

| Lot | (microns) | | | Apparent Density | Hall Flow (s) |
|---|---|---|---|---|---|
| | D10 | D50 | D90 | | |
| A2 | 7 | 12 | 21 | 9.3 | 7.3 |
| B2 | 43 | 64 | 100 | 9.9 | 5.6 |
| C2 | 47 | 69 | 103 | 9.6 | 5.7 |
| D2 | 7 | 13 | 21 | 9.5 | 9.8 |
| E2 | 16 | 26 | 40 | 9.6 | 6.2 |
| F2 | 17 | 26 | 42 | 9.6 | 6.0 |

Example 5

In this example, several tantalum tensile bars in the shape of cylindrical bars or rods were made. The bars or rods has two flat ends with the cylindrical shape between. Sample 5.1 was a comparative example wherein a wrought tantalum bar was made by vacuum arc melting of tantalum nodular powder (commercially sold as KDEL from Global Advanced Metals USA, Inc) in a mold.

Figure 3:
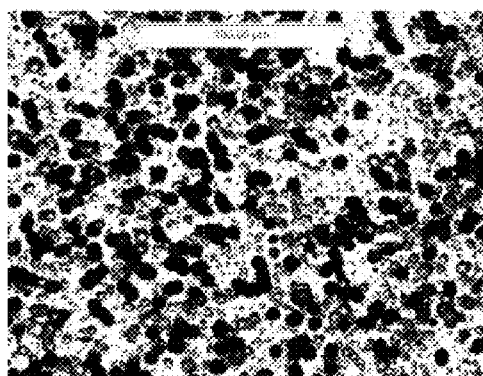
FIGS. 3 to 10 are SEM photographs of the microstructure of tensile bars made from spherical tantalum powder of the present invention.

Sample 5.2 was a tantalum tensile bar formed from the KDEL tantalum powder. The powder was pressed into a green log at a pressure of about 30,000 psi to 50,000 psi and sintered at a temperature of 2500 deg C. to 3000 deg C. for 3 hrs to form a sintered powder-met bar. FIG. 3 is a SEM photograph of the microstructure.

Also, as further explained below, tantalum powder was used in a 3D printing or additive manufacturing process. Specifically, tantalum builds were performed on a laser powder bed fusion machine mm and having a maximum laser power of 400 W. Various base plates were used including Type 316 austenitic chromium nickel stainless steel and Ti alloy (Ti-6V-4Al).

In this example, the spheroidized tantalum powders of Example 4 (various lots) were used for Laser Powder Bed (L-PBF) printing to form fully dense tensile bars. Specifically, tensile bars were printed with 1 mm oversize to standard dimensions (ASTM E8). Powder from Lot A2 was used to print tensile bars T1 through T6, powder from Lot E2 was used to print tensile bar T13 and powder from Lot F2 was used to print tensile bar T14 (see Table 6). The bars were machined to final dimensions on a lathe. Tensile properties were measured on an Instron 4210 Tensile Tester. Tensile bars were analyzed for microstructure and hardness. For microstructure analysis (FIGS. 3-10), the samples were mounted in epoxy, and cut with a diamond saw. The mounted samples were polished and etched in acid and the grains were characterized on a Unition Versamet 2 metallographic microscope. Microhardness was tested using a LECO LM700-AT Tester with AMH32 Software.

The printing parameters and laser parameters used were optimized to produce fully dense parts. The results included a >99.5% density with good overhang in the test build. A cube (25 mm×25 mm×25 mm) with alternating open mesh and solid portions was printed as well in this experiment and this demonstration part showed high resolution (<30 um) of features with the ability to successfully print open cellular structures. This alternating mesh-solid structure is often required for light weight aerospace components and industrial parts, as well as for medical implants to allow improved osteointegration.

Figure 4:
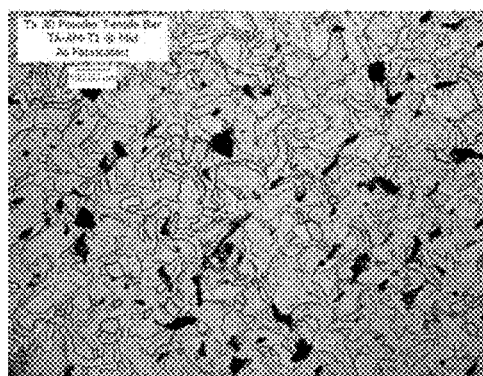
Figure 11:
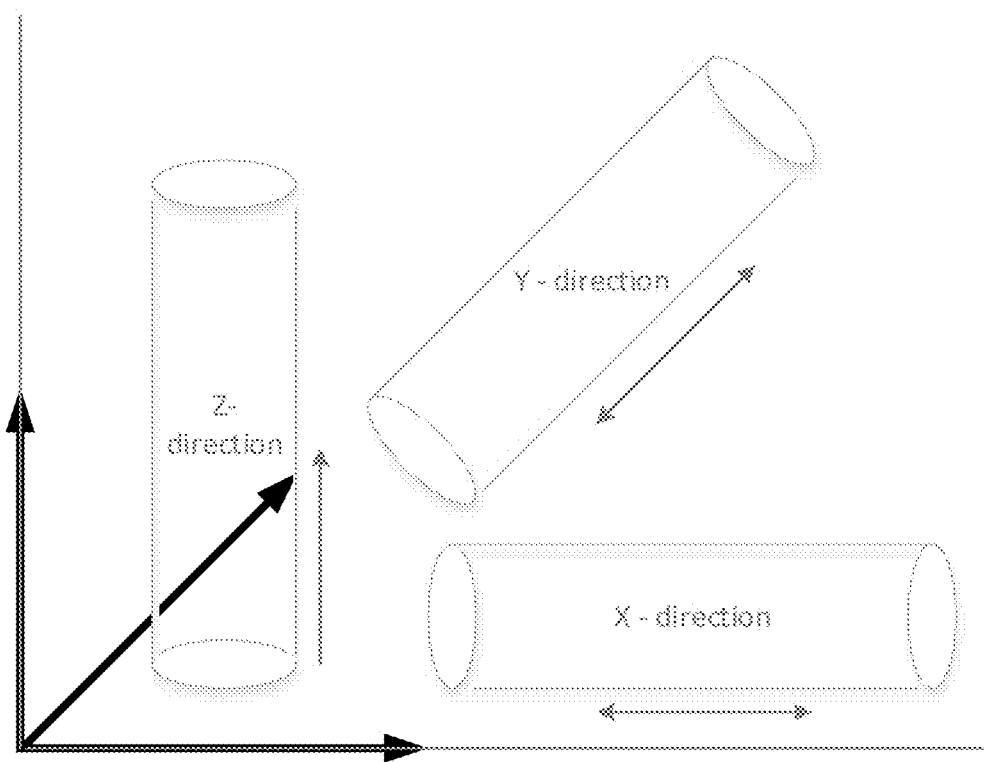
FIG. 11 is an illustration of a cylindrical bar or rod showing the direction and orientation of the 3D printing of the bar/rod -z direction, x direction, and y direction.

Sample 5.3 (Sample T1 in Table 8) was a tantalum tensile bar formed a 3D printing or additive manufacturing process. Specifically, tantalum builds were performed on a Trumpf TruPrint 1000 with a build volume of Dia. 100×100 mm and maximum laser power of 175 W. The base plate used was Type 316 austenitic chromium nickel stainless steel. For Sample 5.3, the cylindrical bar or rod was printed in the z-direction (see FIG. 11), meaning a flat end was formed on the base plate and the cylindrical body was formed upright so that when finished, the bar or rod was upright as the one flat end was at the base of the support plate. Sample 5.3 was not subjected to any heat treatment after being printed. FIG. 4 is a SEM photograph of the microstructure.

Figure 5:
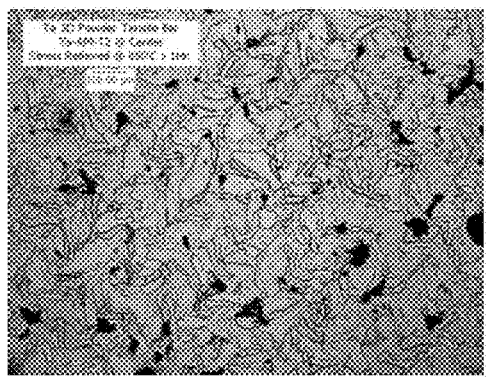
Figure 6:
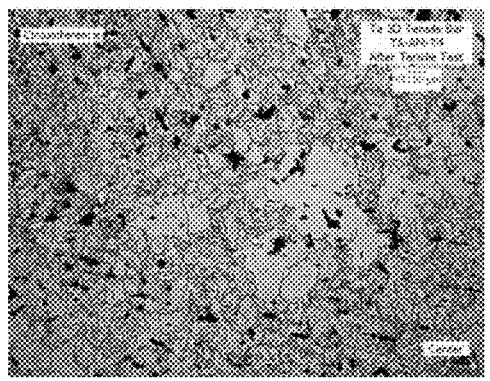

Sample 5.4 (Sample T2 in Table 8) was a tantalum tensile bar formed a 3D printing or additive manufacturing process. Specifically, tantalum builds were performed on a Trumpf TruPrint 1000 with a build volume of Dia. 100×100 mm and maximum laser power of 175 W. The base plate used was Type 316 austenitic chromium nickel stainless steel. For Sample 5.4, the cylindrical bar or rod was printed in the z-direction. Sample 5.4 was subjected to a heat treatment (stress relieved) of 850 deg C. for 1 hour in an air furnace after being printed. FIG. 5 is a SEM photograph of the microstructure Sample 5.5 (Sample T4 in Table 8) was a tantalum tensile bar formed a 3D printing or additive manufacturing process. Specifically, tantalum builds were performed on a Trumpf TruPrint 1000 with a build volume of Dia. 100×100 mm and maximum laser power of 175 W. The base plate used was Type 316 austenitic chromium nickel stainless steel. For Sample 5.5, the cylindrical bar or rod was printed in the z-direction. Sample 5.5 was subjected to a heat treatment (stress relieved) of 1300 deg C. for 1 hour in an air furnace after being printed. FIG. 6 is a SEM photograph of the microstructure.

Sample 5.6 (Sample T5 in Table 8) was a tantalum tensile bar formed a 3D printing or additive manufacturing process.

Figure 7:
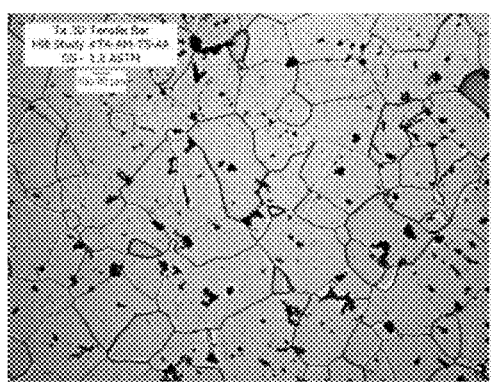

Specifically, tantalum builds were performed on a Trumpf TruPrint 1000 with a build volume of Dia. 100×100 mm and maximum laser power of 175 W. The base plate used was Type 316 austenitic chromium nickel stainless steel. For Sample 5.6, the cylindrical bar or rod was printed in the z-direction. Sample 5.6 was subjected to a heat treatment (stress relieved) of 1700 deg C. for 2 hours in an air furnace after being printed. FIG. 7 is a SEM photograph of the microstructure.

Figure 8:
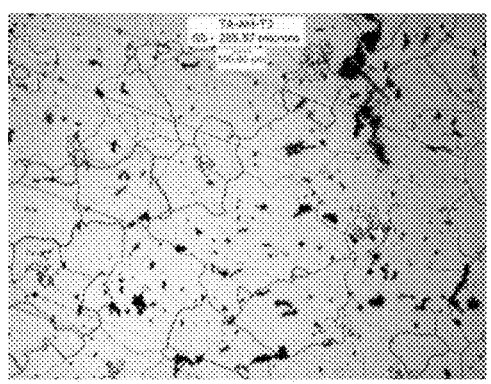

Sample 5.7 (Sample T6 in Table 8) was a tantalum tensile bar formed a 3D printing or additive manufacturing process. Specifically, tantalum builds were performed on a Trumpf TruPrint 1000 with a build volume of Dia. 100×100 mm and maximum laser power of 175 W. The base plate used was Type 316 austenitic chromium nickel stainless steel. For Sample 5.7, the cylindrical bar or rod was printed in the z-direction. Sample 5.7 was subjected to a heat treatment (stress relieved) of 2000 deg C. for 2 hours in an air furnace after being printed. FIG. 8 is a SEM photograph of the microstructure.

Figure 9:
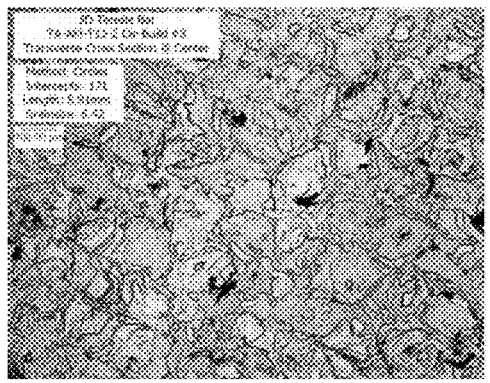

Sample 5.8 (Sample T13 in Table 8) was a tantalum tensile bar formed a 3D printing or additive manufacturing process. Specifically, tantalum builds were performed on a EOS M290 with a build volume of 250 mm×250 mm×325 mm and maximum laser power of 400 W. The base plate used was titanium alloy (Ti-6Al-4V). For Sample 5.8, the cylindrical bar or rod was printed in the z-direction. Sample 5.8 was not subjected to any heat treatment after being printed. FIG. 9 is a SEM photograph of the microstructure.

Figure 10:
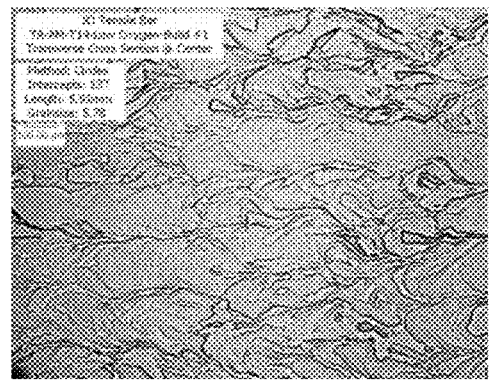

Sample 5.9 (Sample T14 in Table 8) was a tantalum tensile bar formed a 3D printing or additive manufacturing process. Specifically, tantalum builds were performed on a EOS M290 with a build volume of 250 mm×250 mm×325 mm and maximum laser power of 400 W. The base plate used was titanium alloy (Ti-6Al-4V). For Sample 5.9, the cylindrical bar or rod was printed in the x-direction. Sample 5.9 was not subjected to any heat treatment after being printed. FIG. 10 is a SEM photograph of the microstructure.

Further details of each of the Samples are set forth in Table 8 below. Further, tensile properties were measured on an Instron 4210 Tensile Tester.

As can be seen in Table 8, the hardness (Vickers) was significantly higher in the present invention's samples 5.3 through 5.9 compared to sample 5.1 and sample 5.2. The results in Table 8 further show how tensile strength, Yield, and elongation can vary depending on the 3D printing direction (x direction or y direction or z direction) and/or how heat treatment (stress relieving) and/or the oxygen content of the powder.

Compared to wrought tantalum and sinter bar (Table 8), the present invention's tensile bars showed high yield strength (YS) and slightly lower elongation for high oxygen feed powder. Elongation properties were improved after annealing (T4 through T6) without decreasing YS. Elongation was significantly improved by reducing oxygen impurity (T14) without substantial reduction in UTS. Tensile data for T14 showed cup-cone fracture surface typical of ductile failure modes (FIG. 10).

TABLE 8

| Sample | Heat Treat Temperature, deg. C. | UTS, KSI | Yield, KSI | Elongation, % | Hardness, Vickers-200 | Gas impurities, ppm | | | |
|---|---|---|---|---|---|---|---|---|---|
| | | | | | | C | O | N | H |
| Wrought Ta (ref.) | RT | 40 | 25 | 50 | 35 Rockwell | 20 | 72 | 15 | 9 |
| Sinter Bar (ref.) | RT | 77 | 67 | 20 | 194 | 27 | 93 | 6 | 4 |
| T1 | RT | 96 | 41 | 4 | 237 | 24 | 1422 | 23 | 12 |
| T2 | 850 | 94 | 45 | 4 | 276 | 11 | 1100 | 49 | 2 |
| T4 | 1300 | 84 | 80 | 1 | 270 | 21 | 1119 | 50 | 3 |
| T5 | 1700 | 98 | 85 | 17 | 296 | 28 | 966 | 34 | <1 |
| T6 | 2000 | 96 | 84 | 19 | 279 | 16 | 1020 | 44 | 4 |
| T13 | RT | 58 | 55 | 12 | 215 | 19 | 349 | 32 | 10 |
| T14 | RT | 92 | 87 | 35 | 149 | 16 | 107 | 38 | 4 |

All tensile measurements conducted at room temperature

The present invention includes the following aspects/embodiments/features in any order and/or in any combination:

1. Tantalum powder comprising
   a. a spherical shape wherein the powder has an average aspect ratio of from 1.0 to 1.25;
   b. a purity of tantalum of at least 99.99 wt % Ta based on total weight of said tantalum powder, excluding gas impurities;
   c. an average particle size of from about 0.5 micron to about 250 microns;
   d. a true density of from 16 g/cc to 16.6 g/cc;
   e. an apparent density of from about 4 g/cc to about 12.3 g/cc; and
   f. a Hall flow rate of 20 sec or less.
2. The tantalum powder of any preceding or following embodiment/feature/aspect, wherein said tantalum powder is plasma heat-treated.
3. The tantalum powder of any preceding or following embodiment/feature/aspect, wherein said tantalum powder has an oxygen level of less than 400 ppm.
4. The tantalum powder of any preceding or following embodiment/feature/aspect, wherein said tantalum powder has an oxygen level of from 20 ppm to 250 ppm.
5. The tantalum powder of any preceding or following embodiment/feature/aspect, wherein said tantalum powder wherein said average aspect ratio is from 1.0 to 1.1.
6. The tantalum powder of any preceding or following embodiment/feature/aspect, wherein said tantalum powder wherein said average aspect ratio is from 1.0 to 1.05.
7. The tantalum powder of any preceding or following embodiment/feature/aspect, wherein said purity is at least 99.995 wt % Ta.
8. The tantalum powder of any preceding or following embodiment/feature/aspect, wherein said average particle size is from about 0.5 micron to about 10 microns.
9. The tantalum powder of any preceding or following embodiment/feature/aspect, wherein said average particle size is from about 5 microns to about 25 microns.
10. The tantalum powder of any preceding or following embodiment/feature/aspect, wherein said average particle size is from about 15 microns to about 45 microns.
11. The tantalum powder of any preceding or following embodiment/feature/aspect, wherein said average particle size is from about 35 microns to about 75 microns.
12. The tantalum powder of any preceding or following embodiment/feature/aspect, wherein said average particle size is from about 55 microns to about 150 microns.
13. The tantalum powder of any preceding or following embodiment/feature/aspect, wherein said average particle size is from about 105 microns to about 250 microns.
14. The tantalum powder of any preceding or following embodiment/feature/aspect, wherein said tantalum powder has at least one of the following properties:
   a. a D10 size of from about 5 microns to 25 microns;
   b. a D90 size of from about 20 microns to 80 microns; and/or
   c. an oxygen content of from about 100 ppm to about 1000 ppm, such as from about 100 ppm to about 250 ppm.
15. An article comprising the tantalum powder of any preceding or following embodiment/feature/aspect.
16. The article of any preceding or following embodiment/feature/aspect, wherein said article is a boss for a coil set for a physical vapor deposition process.
17. The article of any preceding or following embodiment/feature/aspect, wherein said boss comprises open cellular structures and solid structures.
18. The article of any preceding or following embodiment/feature/aspect, wherein said article is a coil set or part thereof for a physical vapor deposition process.
19. The article of any preceding or following embodiment/feature/aspect, wherein said article is an orthopedic implant or part thereof.
20. The article of any preceding or following embodiment/feature/aspect, wherein said article is a dental implant.
21. A method for forming an article, said method comprising additive manufacturing said article by utilizing the tantalum powder of any preceding or following embodiment/feature/aspect to form the shape of said article or part thereof.
22. The method of any preceding or following embodiment/feature/aspect, wherein said additive manufacturing comprises laser powder bed fusion.
23. The method of any preceding or following embodiment/feature/aspect, wherein said additive manufacturing comprises electron beam powder bed fusion.
24. The method of any preceding or following embodiment/feature/aspect, wherein said additive manufacturing comprises directed energy deposition.
25. The method of any preceding or following embodiment/feature/aspect, wherein said additive manufacturing comprises laser cladding via a powder or wire.
26. The method of any preceding or following embodiment/feature/aspect, wherein said additive manufacturing comprises material jetting.
27. The method of any preceding or following embodiment/feature/aspect, wherein said additive manufacturing comprises sheet lamination.
28. The method of any preceding or following embodiment/feature/aspect, wherein said additive manufacturing comprises vat photopolymerization.
29. A method to make to the tantalum powder of any preceding or following embodiment/feature/aspect, said method comprising:
   a. plasma heat-treating a starting tantalum powder to at least partially melt at least an outer surface of said starting tantalum powder in an inert atmosphere to obtain a heat-treated tantalum powder, and
   b. cooling said heat-treated tantalum powder in an inert atmosphere to obtain said tantalum powder.
30. The method of any preceding or following embodiment/feature/aspect, wherein said starting tantalum powder is sodium-reduced tantalum powder.
31. The method of any preceding or following embodiment/feature/aspect, wherein said starting tantalum powder is a basic lot tantalum powder.
32. The method of any preceding or following embodiment/feature/aspect, wherein said starting tantalum powder has a first particle size distribution, and said tantalum powder has a second particle size distribution, and said first particle size distribution and said second particle size distribution are within 10% of each other.
33. The method of any preceding or following embodiment/feature/aspect, wherein prior to step a, the starting tantalum powder is formed by sintering a first tantalum powder to obtain a sintered powder, and then e-beam melting of said sintered powder to obtain an ingot, and then reducing said ingot to said starting tantalum powder.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for forming an article or a part thereof, said method comprising additive manufacturing said article or said part thereof by utilizing a powder that is a tantalum powder to form the shape of said article or said part thereof, wherein the powder comprises at least the following properties:
    a. a spherical shape wherein the powder has an average aspect ratio of from 1.0 to 1.25;
    b. a purity of tantalum of at least 99.99 wt % Ta based on total weight of tantalum present in the powder, excluding gas impurities;
    c. an average particle size of from about 0.5 micron to about 250 microns;
    d. an apparent density from about 4 g/cc to about 12.3 g/cc;
    e. a true density of from 16 g/cc to 16.6 g/cc; and
    f. a Hall flow rate of 20 sec or less,
    and wherein one or more of the following properties is achieved in forming said article or said part thereof: a) ultimate tensile strength (UTS) is at least 50% greater than wrought Ta of the same shape, b) the UTS is over 50 KSI, c) a Yield Stress that is at least 50% greater than wrought Ta of the same shape, d) the Yield Stress is over 35 KSI, e) an elongation from about 1% to about 50%.

2. The method of claim 1, wherein said powder has an oxygen level of less than 100 ppm.

3. The method of claim 1, wherein said powder has an oxygen level of from 20 ppm to 100 ppm.

4. The method of claim 1, wherein said powder wherein said average aspect ratio is from 1.0 to 1.05.

5. The method of claim 1, wherein the powder is tantalum powder having a purity of at least 99.9995 wt % Ta.

6. The method of claim 1, wherein said average particle size is from about 0.5 micron to about 10 microns.

7. The method of claim 1, wherein said average particle size is from about 5 microns to about 25 microns.

8. The method of claim 1, wherein said average particle size is from about 15 microns to about 45 microns.

9. The method of claim 1, wherein said average particle size is from about 35 microns to about 75 microns.

10. The method of claim 1, wherein said average particle size is from about 55 microns to about 150 microns.

11. The method of claim 1, wherein said average particle size is from about 105 microns to about 250 microns.

12. The method of claim 1, wherein said tantalum powder has at least one of the following properties:
    a. a D10 size of from about 5 microns to 25 microns;
    b. a D90 size of from about 20 microns to 80 microns.

13. The method of claim 1, wherein said additive manufacturing comprises laser powder bed fusion.

14. The method of claim 1, wherein said additive manufacturing comprises electron beam powder bed fusion.

15. The method of claim 1, wherein said additive manufacturing comprises directed energy deposition.

16. The method of claim 1, wherein said additive manufacturing comprises laser cladding via a powder or wire.

17. The method of claim 1, wherein said additive manufacturing comprises material jetting.

18. The method of claim 1, wherein said additive manufacturing comprises sheet lamination.

19. The method of claim 1, wherein said additive manufacturing comprises vat photopolymerization.

20. The method of claim 1, wherein the article is a medical or dental implant.

21. The method of claim 1, wherein the article is an orthopedic implant for a replacement of a hand, ankle, shoulder, hip, knee, bone, total joint reconstruction (arthroplasty), cranial facial reconstruction, or spinal.

22. The method of claim 1, wherein the article is a dental implant for facial reconstruction that is a mandible or maxilla.

23. The method of claim 1, wherein the article is a medical marker.

24. The method of claim 1, wherein the article is a surgical tool or said part thereof, an augment, or an aerospace part.

25. The method of claim 1, where the additive manufacturing comprises laser metal deposition (LMD), gas-metal arc welding, plasma welding, cold spraying, metal injection molding, plasma additive manufacturing, thermal spraying, electron beam melting, or a powder bed fusion process using an electron beam in a vacuum.

26. The method of claim 1, wherein the additive manufacturing utilizes a device having one or more of the following settings: a laser power of from 150 W to about 175 W; a scan speed of from about 100 mm/s to about 500 mm/s; hatch spacing of from about 30 microns to about 100 microns; a layer thickness of from about 10 microns to about 50 microns; and/or an energy density of from about 3 J/mm$^2$ to about 20 J/mm$^2$.

27. The method of claim 1, wherein the additive manufacturing includes utilizing a baseplate.

28. The method of claim 27, wherein the baseplate is a tantalum baseplate, a titanium alloy baseplate, a stainless steel baseplate, or a stainless steel alloy baseplate.

29. The method of claim 1, wherein the method further comprises annealing the article.

30. The method of claim 1, wherein the method further comprises annealing the article at a temperature of from about 800 deg C. to about 2,000 deg C. for 10 mins to 10 hours.

31. The method of claim 1, wherein all of the properties a)-d) are achieved.

32. The method of claim 1, wherein the powder has an oxygen content of from about 20 ppm to 200 ppm, an oxygen (in ppm) to BET (in $m^2/g$) ratio of from about 2,000 to about 4,000, a carbon content of from about 1 ppm to about 100 ppm, a nitrogen content of from about 5 ppm to 5,000 ppm, a hydrogen content of from about 1 ppm to about 1,000 ppm, an iron content of from about 1 ppm to about 50 ppm, a nickel content of from about 1 ppm to about 150 ppm, a chromium content of from about 1 ppm to about 100 ppm, a sodium content of from about 0.1 ppm to about 50 ppm, a potassium content of from about 0.1 ppm to about 100 ppm, a magnesium content of from about 1 ppm to about 50 ppm, a phosphorus (P) content of from about 1 ppm to about 500 ppm, and a fluoride (F) content of from about 1 ppm to about 500 ppm.

33. The method of claim 1, wherein the powder has a particle size distribution (based on overall %) as follows, based on mesh size:
  +60 # of from about 0.0 to about 0.5%,
  60/170 of from about 45% to about 70%,
  170/325 of from about 20% to about 50%,
  325/400 of from about 1.0% to about 10%, and
  −400 of from about 0.1 to about 2.0%.

34. A method for forming an article or a part thereof, said method comprising additive manufacturing said article or said part thereof by utilizing a powder that is a tantalum alloy powder to form the shape of said article or said part thereof, wherein the powder comprises at least the following properties:
  a. a spherical shape wherein the powder has an average aspect ratio of from 1.0 to 1.25;
  b. an average particle size of from about 0.5 micron to about 250 microns;
  c. an apparent density from about 4 g/cc to about 12.3 g/cc; and
  d. a Hall flow rate of 20 sec or less.

35. The method of claim 34, wherein the tantalum alloy powder contains a) at least tantalum metal and b) i) one or more other metals and/or ii) non-metal elements and/or iii) metalloid elements.

36. The method of claim 35, wherein the one or more other metals and/or the non-metal elements and/or the metalloid elements is Ti, Nb, Si, W, Mo, Re, Rh, V, Th, Zr, Hf, Cr, Mn, Sc, Y, C, B, Ni, Fe, Co, Al, Sn, Au, Th, U, Pu, and/or rare earth element(s).

37. The method of claim 34, wherein the tantalum alloy powder is a Ta—Ti alloy or a Ta—Si alloy or Ta—W alloy or Ta—Mo alloy or Ta—Nb alloy.

38. The method of claim 35, wherein tantalum is the metal present in the highest percent based on the weight of the tantalum alloy powder, as compared to the one or more other metals.

* * * * *